United States Patent
Mao et al.

(10) Patent No.: US 8,354,523 B2
(45) Date of Patent: Jan. 15, 2013

(54) OLIGONUCLEOTIDE PROBES AND USES THEREOF

(75) Inventors: Fei Mao, Fremont, CA (US); Xing Xin, Foster City, CA (US)

(73) Assignee: Allelogic Biosciences Corporation, Hayward, CA (US)

( * ) Notice: Subject to any disclaimer, the term of this patent is extended or adjusted under 35 U.S.C. 154(b) by 575 days.

(21) Appl. No.: 12/307,358

(22) PCT Filed: Jul. 19, 2007

(86) PCT No.: PCT/US2007/016500
§ 371 (c)(1),
(2), (4) Date: Oct. 26, 2009

(87) PCT Pub. No.: WO2009/038548
PCT Pub. Date: Mar. 26, 2009

(65) Prior Publication Data
US 2010/0086916 A1    Apr. 8, 2010

Related U.S. Application Data

(60) Provisional application No. 60/832,025, filed on Jul. 19, 2006.

(51) Int. Cl.
*C07H 19/04* (2006.01)
*C12Q 1/68* (2006.01)
*C12P 19/34* (2006.01)

(52) U.S. Cl. ....... 536/26.6; 435/6.1; 435/91.1; 435/91.2

(58) Field of Classification Search .............. 435/6.1, 435/91.1, 91.2; 536/26.6
See application file for complete search history.

(56) References Cited

FOREIGN PATENT DOCUMENTS

| EP | 0229943 A2 | 7/1987 |
|----|------------|--------|
| EP | 0229943 A3 | 11/1987 |

OTHER PUBLICATIONS

Stratagene catalog, p. 39, 1988.*
Cardullo, et al. Detection of nucleic acid hybridization by nonradiative fluorescence resonance energy transfer. Proc Natl Acad Sci U S A. Dec. 1988;85(23):8790-4.
International search report and written opinion dated Sep. 11, 2008 for PCT Application No. US07/16500.

* cited by examiner

*Primary Examiner* — Jezia Riley
(74) *Attorney, Agent, or Firm* — Wilson Sonsini Goodrich & Rosati

(57) ABSTRACT

The present invention provides a dually labeled oligonucleotide probe, methods of preparing and using the same. The subject probes are particularly useful for high-sensitive nucleic acid detection via hybridization assays including but not limited to template-directed polymerization reactions.

21 Claims, 12 Drawing Sheets

SEQUENCE LISTING

<160> NUMBER OF SEQ ID NOS: 58

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
catccatgac aactttggta tcgt                                          24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagtcttctg ggtggcagtg a                                             21

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcatggact gtggtcatga gtccttc                                       27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
gaaggactca tgaccacagt ccatgcc                                       27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
gaaggactca tgaccacagt ccatgcc                                       27

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6

```
ggactcatga ccacagtcca tgcc                                          24
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7

```
ctcatgacca cagtccatgc c                                             21
```

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8

```
catgaccaca gtccatgcc                                                19
```

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9

```
catgaccaca gtccatgcc                                                19
```

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10

```
gaaggactca tgaccacagt ccatgcc                                       27
```

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11

```
ggactcatga ccacagtcca tgcc                                          24
```

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12

```
ctcatgacca cagtccatgc c                                             21
```

```
<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
catgaccaca gtccatgcc                                                    19

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gaccacagtc catgcc                                                       16

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgcaggctac catccatgtc                                                   20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cctaccaact gtgggtcatc ct                                                22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ctgcccagca tgaagatggc cc                                                22

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gcccagcatg aagatggccc                                                   20

<210> SEQ ID NO 19
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
gcccagcatg aagatggc                                                       18

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tctctgaagg gagtttctcc aatt                                                24

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttcacacagt ggtttggctt aga                                                 23

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
tttggaccca ccattgcaga gtttcttc                                            28

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
ggacccacca ttgcagagtt tcttc                                               25

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
ggacccacca ttgcagagtt tc                                                  22

<210> SEQ ID NO 25
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 25
ggacccacca ttgcagag                                                  18

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aaatttccca ccatatagaa ggccatatat                                     30

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
ggccttctat atggtggg                                                  18

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
ggccttctat atggtggg                                                  18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ggccttctat atggtggg                                                  18

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
atatatgcgc tcaggaggag caaattt                                        27

<210> SEQ ID NO 31
<211> LENGTH: 15
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 31
gctcctcctg agcgc                                                      15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
gctcctcctg agcgc                                                      15

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tatatacacg acgccagggc tttaaa                                          26

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
gccctggcgt cgtg                                                       14

<210> SEQ ID NO 35
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
gccctggcgt cgtg                                                       14

<210> SEQ ID NO 36
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gggcccaacc aggaaataac tctggctcat aactactaaa gcgcgc                    46

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      probe
```

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
tttagtagtt atgagccaga gttatttcct ggtt                                    34

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
tttagtagtt atgagccaga gttatttcct ggtt                                    34

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
gttatgagcc agagttattt cctgg                                              25

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
gttatgagcc agagttattt cctgg                                              25

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
gagccagagt tatttcctgg                                                    20

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tttaaaagac cccacactac catcggcgct aatatat                                 37

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
tagcgccgat ggtagtgtgg ggtct                                              25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
tagcgccgat ggtagtgtgg ggtct                                              25

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
tagcgccgat ggtagtgtg                                                     19

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
tagcgccgat ggtagtgtgg ggtct                                              25

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
tagcgccgat ggtagtgtgg ggt                                                23

<210> SEQ ID NO 48
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
catccatgac aactttggta tcgtggaagg actcatgacc acagtccatg ccatcactgc        60
cacccagaag actg                                                          74

<210> SEQ ID NO 49
<211> LENGTH: 249
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
gtctagacgg ctcagatagc atacaagaga ccatgcaggc taccatccat gtccctgccc    60
agcatgaaga tggccctgag gatgacccac agttggtagg catcactgct cgtaacattc   120
cacgagggcc ccagttggct gcccagaact tgggcatcag cctggccaac ttgttgctga   180
gcaaaggagc caaaaacatc ctggatgttg cacggcagct taacgatgcc cattaactgg   240
tttgtgggg                                                           249
```

<210> SEQ ID NO 50
<211> LENGTH: 84
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

```
tctctgaagg gagtttctcc aattatttgg acccaccatt gcagagtttc ttcagttagg    60
tctaagccaa accactgtgt gaac                                           84
```

<210> SEQ ID NO 51
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

```
ccccatgccg aactcagaag tgaaacgccg tagcgccgat ggtagtgtgg ggtctcctca    60
tgcgagagta gggaactgcc aggcat                                         86
```

<210> SEQ ID NO 52
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

```
ccccatgccg aactca                                                    16
```

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53

```
atgcctggca gttccctac                                                 19
```

<210> SEQ ID NO 54
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54

```
catccatgac aactttggta tcgtggaagg actcatgaac acagtccatg ccatcactgc    60
```

```
cacccagaag actg                                                            74

<210> SEQ ID NO 55
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
catccatgac aactttggta tcgtggaagg actcatgatc acagtccatg ccatcactgc           60
cacccagaag actg                                                            74

<210> SEQ ID NO 56
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
catccatgac aactttggta tcgtggaagg actcatgagc acagtccatg ccatcactgc           60
cacccagaag actg                                                            74

<210> SEQ ID NO 57
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
catccatgac aactttggta tcgtggaagg actcatgagc acactccatg ccatcactgc           60
cacccagaag actg                                                            74

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
catgagcaca atccatgcc                                                       19
```

OLIGONUCLEOTIDE PROBES AND USES THEREOF

CROSS-REFERENCE

This application claims the benefit of U.S. Provisional Application No. 60/832,025, filed Jul. 19, 2006, which application is incorporated herein by reference in its entirety.

BACKGROUND OF THE INVENTION

Nucleic acid polymers such as DNA and RNA are essential to the transmission of genetic information from one generation to the next and in the routine functioning of all living organisms. Accordingly these molecules are the objects of intense study and a number of techniques have been developed to study of these molecules. These methods include but are not limited to methods for identifying the presence of a specific polynucleotide sequence in a given sample and methods designed to measure the number of specific nucleic acid molecules originally present in a given sample.

Practical uses for these techniques include identifying specific species and relationships between various species based upon similarities in oligonucleotide sequences. Other uses include diagnosing disease by identifying specific sequences in a given sample as indicative of a given pathology. Still other uses, too numerous to mention, include identifying individuals with a predisposition for developing a specific pathology as well as assessing the efficacy of proposed treatment regimes based on the presence of specific polynucleotides in a given patient's genome.

One of the most widely used and powerful techniques for the study and manipulation of oligonucleotides is the polymerase chain reaction (PCR). PCR is a primer extension reaction that provides a method for amplifying specific nucleic acids in vitro. This technique was first described in 1987. PCR can produce million fold copies of a DNA template in a single enzymatic reaction mixture within a matter of hours, enabling researchers to determine the size and sequence of target DNA. This DNA amplification technique has been widely used for cloning and other molecular biological manipulations. Further discussion of PCR is provided in Mullis et al., *Methods Enzymol.* (1987); and Saiki et al., *Science* (1985).

One PCR based technique that is particularly useful is Quantitative PCR (qPCR). Briefly, the mechanism of qPCR is based on the fact that PCR amplifies a target DNA in an exponential manner. By running a PCR reaction and measuring the total number of DNA copies at given points during the course of the amplification reaction, one can retroactively calculate the amount of starting DNA material.

Various methods have been developed for determining the amount of PCR product made without having to stop the PCR run or even to sample the reaction during a given PCR run. One such method follows the course of the PCR run in real time by measuring the amount of product at each cycle of DNA synthesis. This process is referred to as real-time PCR. Because of its great sensitivity and because measurements can be made with the sample still in the PCR thermocylcer, various fluorescence-based assays that monitor the formation of PCR products have been developed.

In real-time PCR, a fluorogenic molecule is used to monitor the progress of target DNA amplification. Depending on the mode of signal generation, the fluorogenic molecule may either be a fluorogenically labeled oligonucleotide or a simple fluorogenic DNA-binding dye. Real-time qPCR using a DNA-binding dye is primarily used for research applications while that using an oligonucleotide-based probe is used in diagnostics or applications where highly specific nucleic acid detection is essential. The most widely used fluorogenic probes are commercially called TaqMan® probes, which are oligonucleotides containing a covalently labeled fluorescent reporter dye and a fluorescence quencher molecule. By having its sequence complementary to a target sequence, a TaqMan® robe is capable of binding to a region of the target sequence via hybridization. Before hybridization, a TaqMan® probe assumes a random conformation, in which the fluorescence of the reporter dye is quenched by the fluorescence quencher via fluorescence resonance energy transfer (FRET) due to the proximity of the reporter and quencher molecules. FRET is dependent on the inverse sixth power of the distance between the reporter and quencher. Consequently, the level of fluorescence exhibited by a TaqMan® probe is highly sensitive to the distance between the quencher and the reporter. On hybridization to a target sequence, the reporter dye and the quencher are separated by a longer distance, resulting man increase of fluorescence due to less efficient FRET. The degree of fluorescence increase is proportional to the amount of target DNA present, thereby making it possible to monitor the amount of DNA in real-time as the PCR proceeds. When a PCR is carried out using a DNA polymerase possessing a 5'-exonuclease domain, the hybridized TaqMan® probe will be cleaved by the exonuclease, resulting in the permanent separation of the reporter dye and quencher. Because the reporter dye and quencher are completely separated, the fluorescence of the reporter dye is fully released. For this reason, real-time qPCR relying on the hydrolytic cleavage of a TaqMan® probe is generally more sensitive than that relying on the hybridization of the probe. Since a TaqMan® probe can both monitor the progress of the PCR and verify the identity of the amplified target at the same time, TaqMan®-based real-time qPCR makes a post PCR verification step unnecessary, providing the high specificity required for demanding applications such as medical diagnosis and prognosis. However, TaqMan® probes are usually expensive and time-consuming to synthesize. Furthermore, due to their complex design and the uniqueness of each probe, the quality of TaqMan®-like probes could vary considerably from lab to lab and from batch to batch, potentially leading to inconsistent PCR results from time to time.

Given the importance of oligonucleotide-based probes, there remains a considerable need for further improved methods for the designs and manufacturing of these probes. One object of the present invention is to provide alternative oligonucleotide-based probes and efficient methods for making and using the same.

SUMMARY OF THE INVENTION

The present invention provides dually labeled oligonucleotide probes useful for detecting target nucleic acid sequences. In one embodiment, the present invention provides a dually labeled oligonucleotide probe that hybridizes to a region in a target sequence, said probe comprising a first dye that is fluorescent and a second dye, separated by at least about 5 nucleotide bases, wherein the two dyes are configured in a manner such that the first dye acts as a reporter that contributes to a fluorescent signal detected after hybridization of the probe with a target nucleic acid, and the second dye acts as a quencher of the first dye; and wherein at least one of the two dyes enhances probe hybridization such that the probe has a calculated melting temperature (calculated Tm) that is no more than 5° C. higher than that of a primer used in conjunction with the probe in amplifying the target sequence in an amplification reaction. In one aspect, the probe has a calculated melting temperature (calculated Tm) that is within ±5° C., inclusive, of the calculated Tm of a primer used in conjunction with the probe in amplifying the target. In another aspect, the probe has a calculated melting temperature (calculated Tm) that is substantially the same or lower as compared to that of a primer used in conjunction with the probe in amplifying the target sequence. The calculated Tm can be ascertained based on the method of SantaLucia setting a salt concentration at 60 mM and a concentration of the oligonucleotide at 500 nm.

In a related but separate embodiment, the present invention provides a dually labeled oligonucleotide probe comprising less than 15 nucleotides that hybridizes to a region in a target sequence, wherein the probe comprises a first dye that is fluorescent and a second dye, the two dyes being configured in a manner such that the first fluorescent dye acts as a reporter that contributes to a fluorescent signal detected after hybridization of the probe with the target nucleic acid, and the second dye acts as a quencher of the first dye; and wherein at least one of the two dyes enhances probe hybridization such that the probe exhibits an observed melting temperature (observed Tm) that is higher than that of a corresponding probe lacking the at least one of the two dyes. In one aspect, the observed Tm is at least about 5° C. higher than that of a corresponding probe lacking the at least one of the two fluorescent dyes. In another aspect, the observed Tm is at least about 10° C. higher than that of a corresponding probe lacking the at least one of the two fluorescent dyes.

Where desired, any of the probes of the present invention may comprise two dyes separately attached to the 5' end and the 3' end. The first dye and the second dye can have the same chemical structure. In some aspects, the second dye contributes to a fluorescent signal detected after hybridization of the probe with a target nucleic acid when the second dye is cleaved from the probe. In other aspects, one of the two dyes is selected from the group consisting of a rhodamine dye, a positively charged cyanine dye, a rosamine dye, an oxazine dye and a thiazine dye. In yet other aspects, the first dye and the second dye are designed to avoid forming a FRET pair. Where desired, the first dye and/or the second dye are attached to an internal base, e.g., thymidine (T). The probes may yield an undetectable gain of, or a decrease in fluorescent intensity when hybridized to a nucleic acid target but before being cleaved by a polymerase used in conjunction in amplifying a target nucleic acid sequence in an amplification reaction. In some instances, at least one of the dyes selected is capable of binding to the minor grooves of a double stranded nucleic acid molecule, with the proviso that such dye is not a 1,2 dihydro [3,2c] indole (CDPI) containing or pentameric N-methylpyrrole-4-carbox-2-amide ($MPC_5$) containing MGB probe.

The present invention also provides a reaction mixture useful for amplification of a nucleic acid target comprising at least one oligonucleotide primer and a subject probe, wherein said primer primes the synthesis of a strand of said target, and wherein the probe hybridizes to a region of said target synthesizable by said primer. The reaction mixture may further comprise a pair of primer (forward and reverse) and/or a nucleic acid polymerase having a 5' to 3' nuclease activity.

The present invention further provides a kit for detecting a nucleic acid sequence comprising a reaction mixture of the present invention and a nucleic acid polymerase.

Also provided is a method for detecting or quantifying a nucleic acid target in an assay. The method comprises a) providing a subject probe; b) contacting said probe with the nucleic acid target so as to allow for hybridization of the probe with the nucleic acid target; and c) detecting or quantifying said nucleic acid target by measuring a change in the fluorescence of the probe upon the hybridization of the nucleic acid probe with the nucleic acid target. In one aspect, the assay is a polymerase chain reaction (PCR). In another aspect, the assay involves the use of a microarray on which one or more nucleic acid target is immobilized. In yet another aspect the assay detects a single nucleotide mismatch between the target and the probe.

Also provided in the present invention is a method of monitoring the increase in a target nucleic acid during amplification of said target, said method comprising: (a) providing an amplification reaction mixture that comprises said target nucleic acid, at least one primer that hybridizes to the target nucleic acid, a labeled oligonucleotide probe that provides a fluorescent signal, the intensity of which is proportional to the increase in the target nucleic acid in the amplification, wherein the probe comprises at least two dyes configured in a manner such that the first dye acts as a reporter contributing to a fluorescent signal detected after hybridization of the probe with a target nucleic acid, and the second dye acts as a quencher of the first label; and wherein at least one of the two dyes enhances probe hybridization such that the probe has a calculated melting temperature (calculated Tm) that is no more than 5° C. higher than that of the at least one primer used in conjunction with the probe in amplifying the target sequence; (b) treating said mixture under conditions for amplifying said target nucleic acid; and (c) measuring the amount of said signal produced by said mixture during said treating step (c).

In a related but separate embodiment, the present invention provides a method of monitoring the increase in a target nucleic acid during amplification of said target. The method comprises the steps of (a) providing an amplification reaction mixture that comprises said target nucleic acid, at least one primer that hybridizes to the target nucleic acid, a labeled oligonucleotide probe having no more than 15 nucleotide bases, wherein the probe provides a fluorescent signal, the intensity of which is proportional to the increase in the target nucleic acid in the amplification, and wherein the probe is characterized in that (i) it comprises at least two dyes configured in a manner such that the first dye acts as a reporter that contributes to a fluorescent signal detected after hybridization of the probe with a target nucleic acid, and the second dye acts as a quencher of the first label; and (ii) wherein at least one of the two dyes enhances probe hybridization such that the probe exhibits an observed melting temperature (observed Tm) that is higher than that of a corresponding probe lacking the at least one of the two dyes; (b) treating said mixture under conditions for amplifying said target nucleic acid; and (c) measuring the amount of said signal produced by said mixture during said treating step (c). In one aspect, at step (c) the amount of signal is determined continuously throughout the amplification reaction. In another aspect, at step (c) the amount of signal is determined intermittently during the amplification reaction.

Further provided in the present invention is a method of preparing a dually labeled probe specific for a nucleic acid target. The method comprises a) selecting a nucleotide sequence complementary to a region of the target; b) selecting at least two fluorescent dyes separated by at least 5 nucleotides to said nucleotide sequence, wherein the two dyes are configured such that the first dye acts as a reporter contributing to a fluorescent signal detected after hybridization of the probe with a target nucleic acid, and the second label acts as a quencher of the first label when the probe is not hybridized with the target nucleic acid; and wherein at least one of the two labels enhances probe hybridization such that the probe has a calculated melting temperature (calculated Tm) that is no more than 5° C. higher than that of a primer used in conjunction with the probe in amplifying the target sequence in an amplification reaction; and c) synthesizing the probe based on the selected nucleotide sequence and the selected dyes.

In a related but separate embodiment, the method of preparing a dually labeled probe specific for a nucleic acid target involves the steps of: a) selecting a nucleotide sequence complementary to a region of the target, said nucleotide sequence comprising less than 15 nucleotide bases; b) selecting at least two fluorescent dyes being configured in a manner such that the first fluorescent dye acts as a reporter contributing to a fluorescent signal detected after hybridization of the probe with the target nucleic acid, and the second dye acts as a quencher of the first dye; and wherein at least one of the two dyes enhances probe-hybridization such that the probe exhibits an observed melting temperature (observed Tm) that is higher than that of a corresponding probe lacking the at least one of the two dyes; and c) synthesizing the probe based on the selected nucleotide sequence and the selected dyes. Any of the subject methods can yield a probe having one or more of features disclosed herein.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

BRIEF DESCRIPTION OF THE FIGURES AND TABLES

Figure 1:
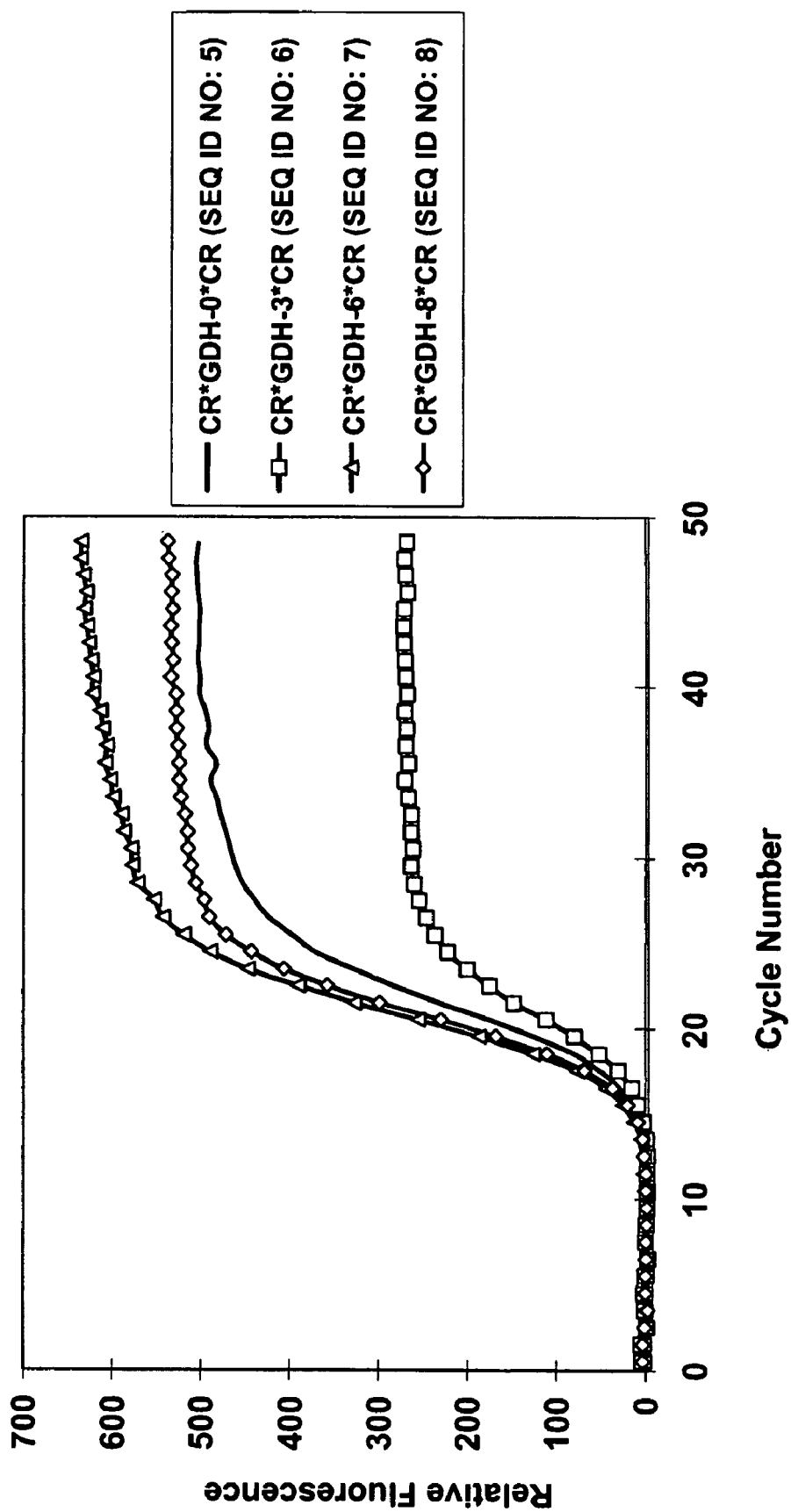

A detailed description of various aspects, features and embodiments of the present invention is provided herein with reference to the accompanying drawings, which are briefly described below. The drawings illustrate various aspects or features of the present invention and may illustrate one or more embodiment(s) or example(s) of the present invention in whole or in part. A reference numeral, letter, and/or symbol that is used in one drawing to refer to a particular element or feature may be used in another drawing to refer to a like element or feature.

FIG. 1 is a graphical representation of amplification plots of probes labeled with 5 carboxyrhodamine 110 designed to hybridize to GDH gene. The graph shows PCR signal comparison between probes of the present invention (SEQ ID NOs 6-8) and a conventional probe (SEQ ID NO 5) in amplifying the GDH gene. All probes are dually labeled with 5-carboxyrhodamine 110 (5-CR110 or CR) at the 5'- and 3'-termini, respectively. The same set of primers was used in all amplifications.

Figure 2:
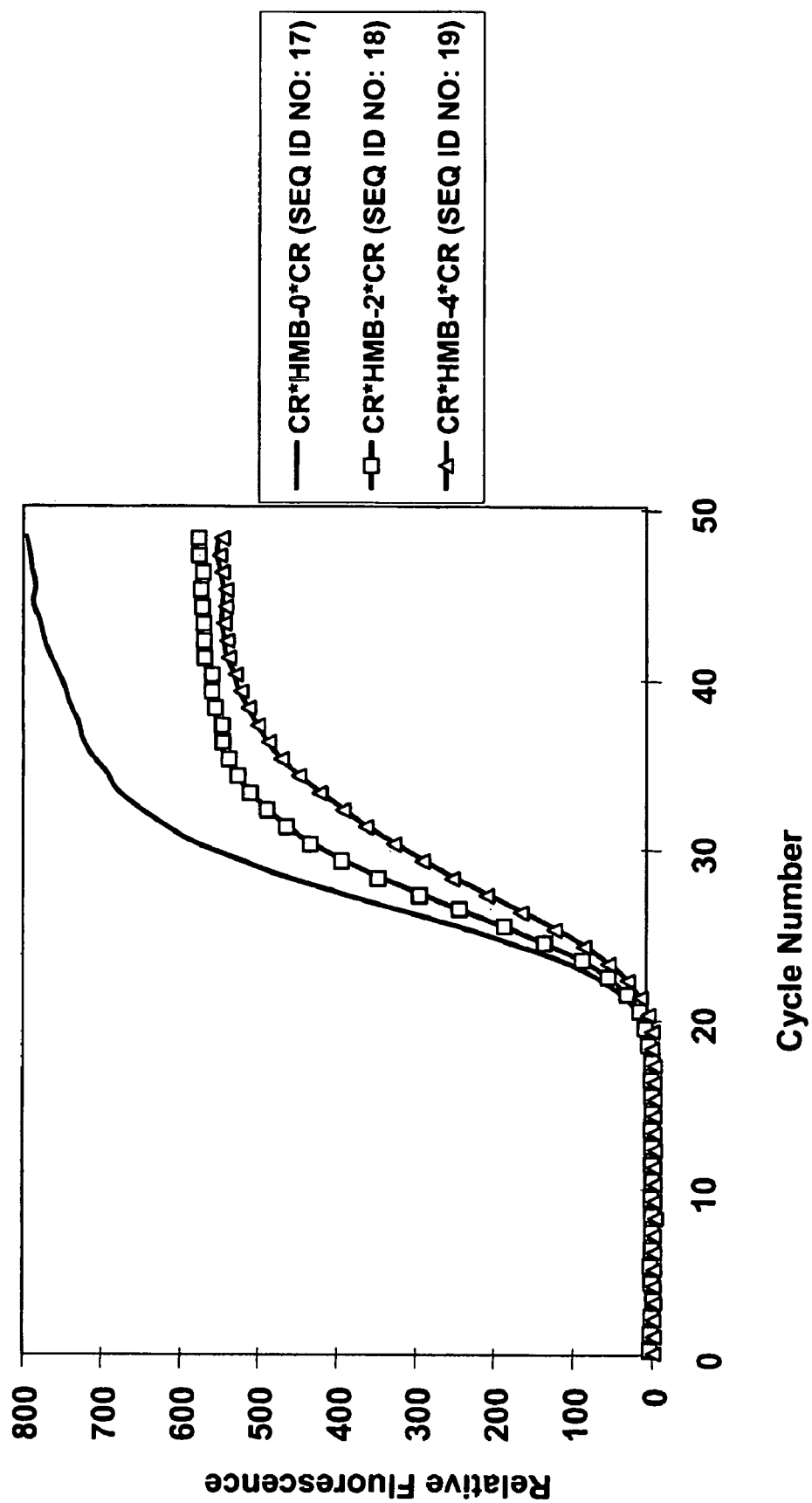

FIG. 2 is a graphical representation of amplification plots of probes designed to hybridize to HMB gene. The figure shows PCR signal comparison between probes according to the present invention (SEQ ID NOs 18 and 19) and a conventional probe (SEQ ID NO 17) in amplifying the HMB gene. All probes are dually labeled with 5-carboxyrhodamine 110 (5-CR110 or CR) at the 5'- and 3'-termini, respectively. The same set of primers was used in all amplifications.

Figure 3:
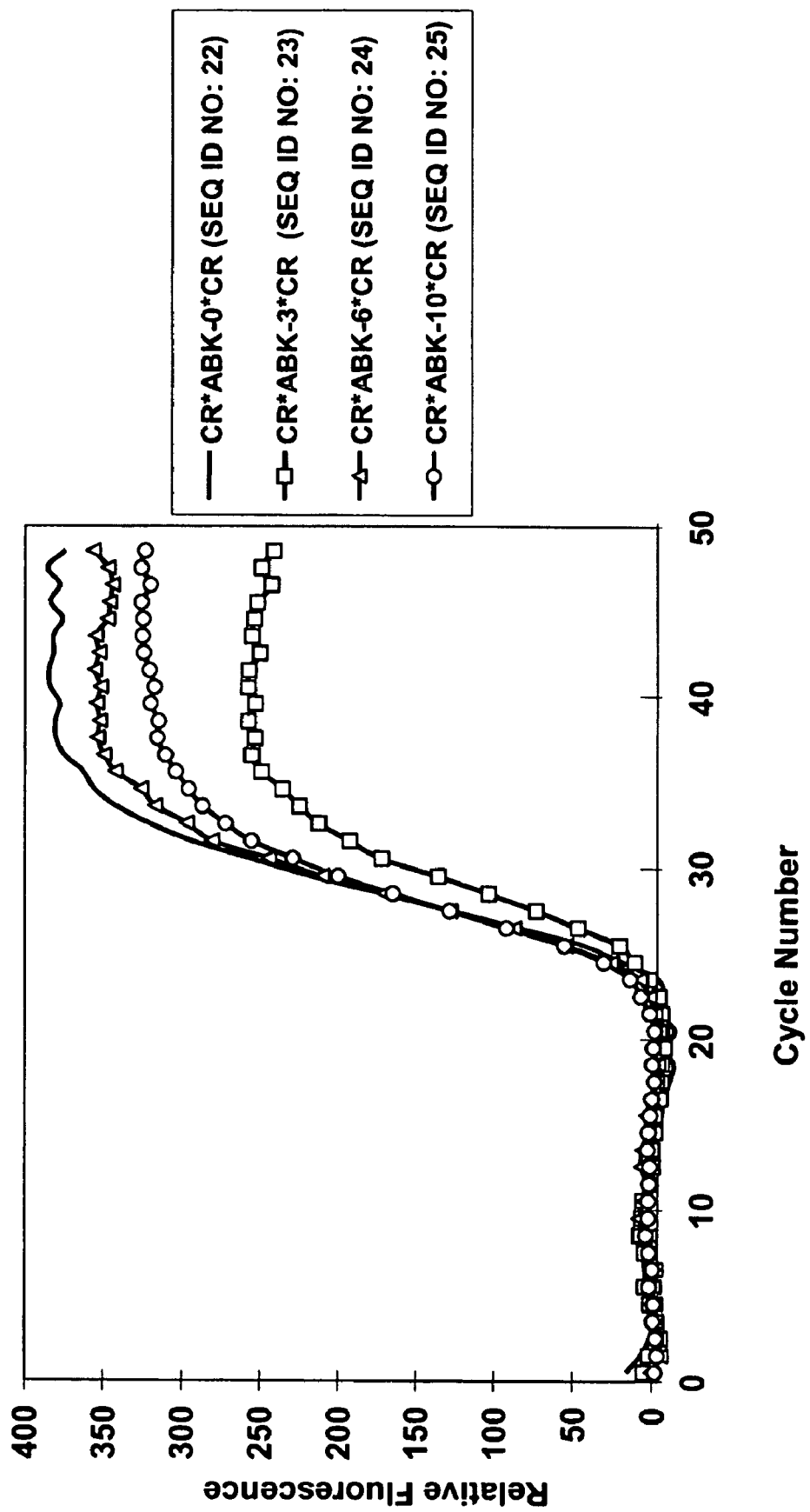

FIG. 3 is a graphical representation of amplification plots of probes designed to hybridize to ABK gene. The figure shows PCR signal comparison between the probes according to the present invention (SEQ ID NOs 23-25) and a conventional probe (SEQ ID NO 22) in amplifications of the ABK gene. All probes are dually labeled with 5-carboxyrhodamine 110 (5-CR110 or CR) at the 5'- and 3'-termini, respectively.

Figure 4:
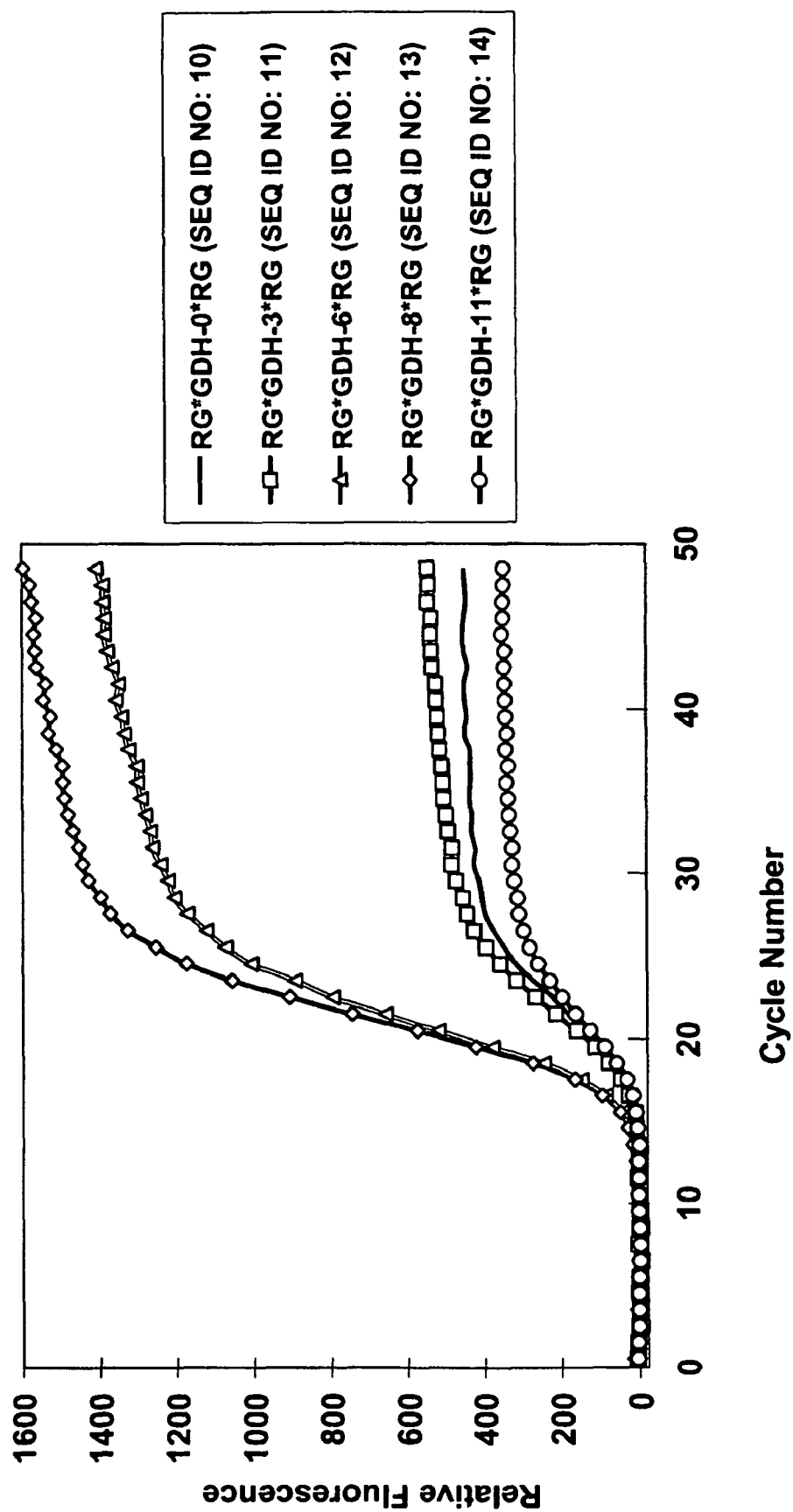

FIG. 4 is a graphical representation of amplification plots of probes designed to hybridize to GDH gene. The figure shows PCR signal comparison between probes according to the present invention (SEQ ID NOs 11-14) and a conventional probe (SEQ ID NO 10) in amplifying the GDH gene. All probes are dually labeled with 6-carboxyrhodamine 6G (R6G or RG) at the 5'- and 3'-termini, respectively.

Figure 5:
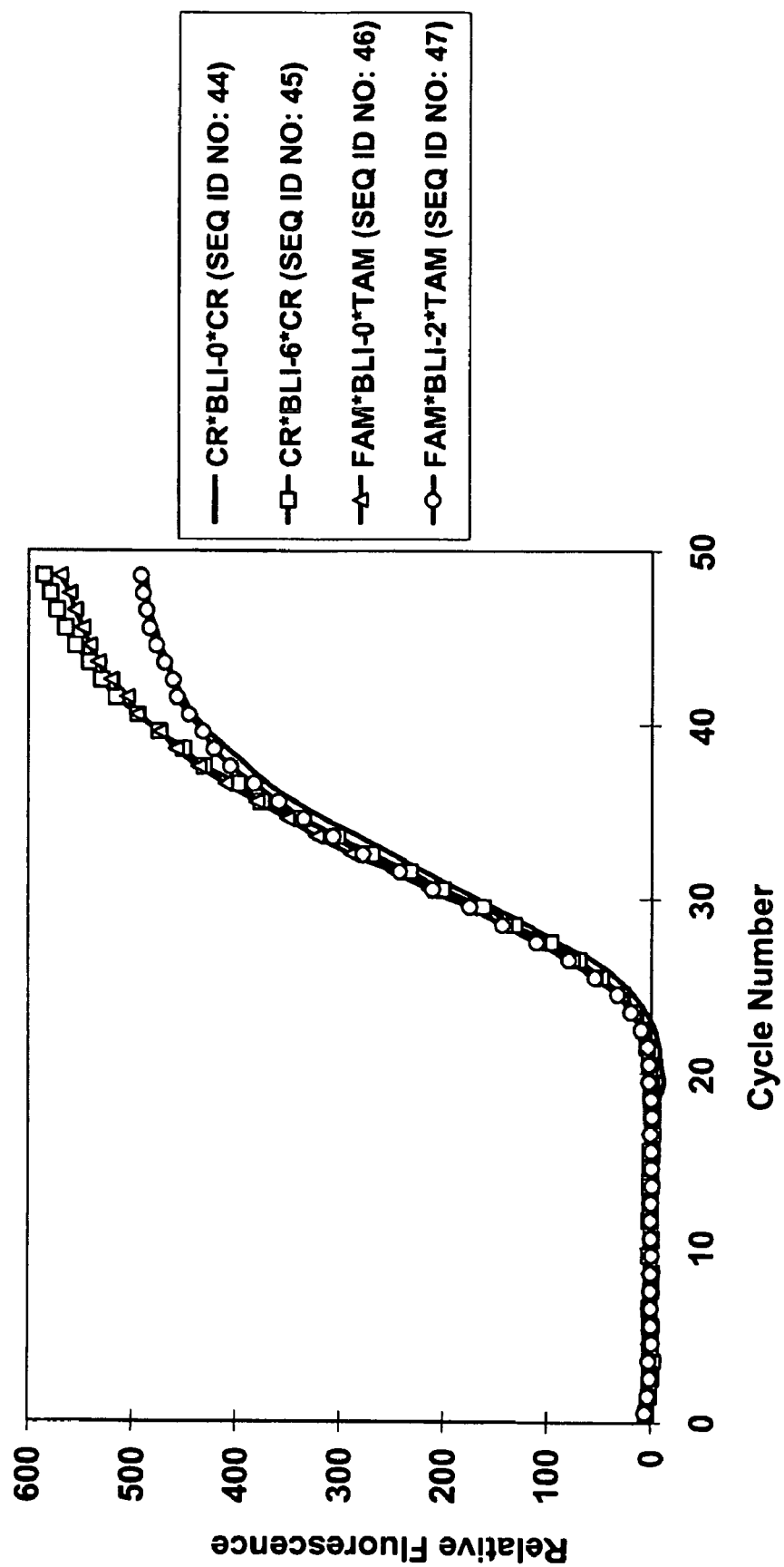

FIG. 5 is a graphical representation of amplification plots of probes designed to hybridize to BLI gene. The figure shows PCR signal comparison between a probe according to the present invention (SEQ ID NO 45) and conventional probes (SEQ ID NOs 44, 46 and 47) in amplifying the BLI gene. Probes of SEQ ID Nos 44 and 45 are dually labeled with 5-CR110 at the 5'- and 3'-termini, respectively. TaqMan® probes of SEQ ID Nos 46 and 47 are each labeled with 5-FAM at the 5'-terminus and 6-tetramethylrhodamine (TAM) at the 3'-terminus.

Figure 6:
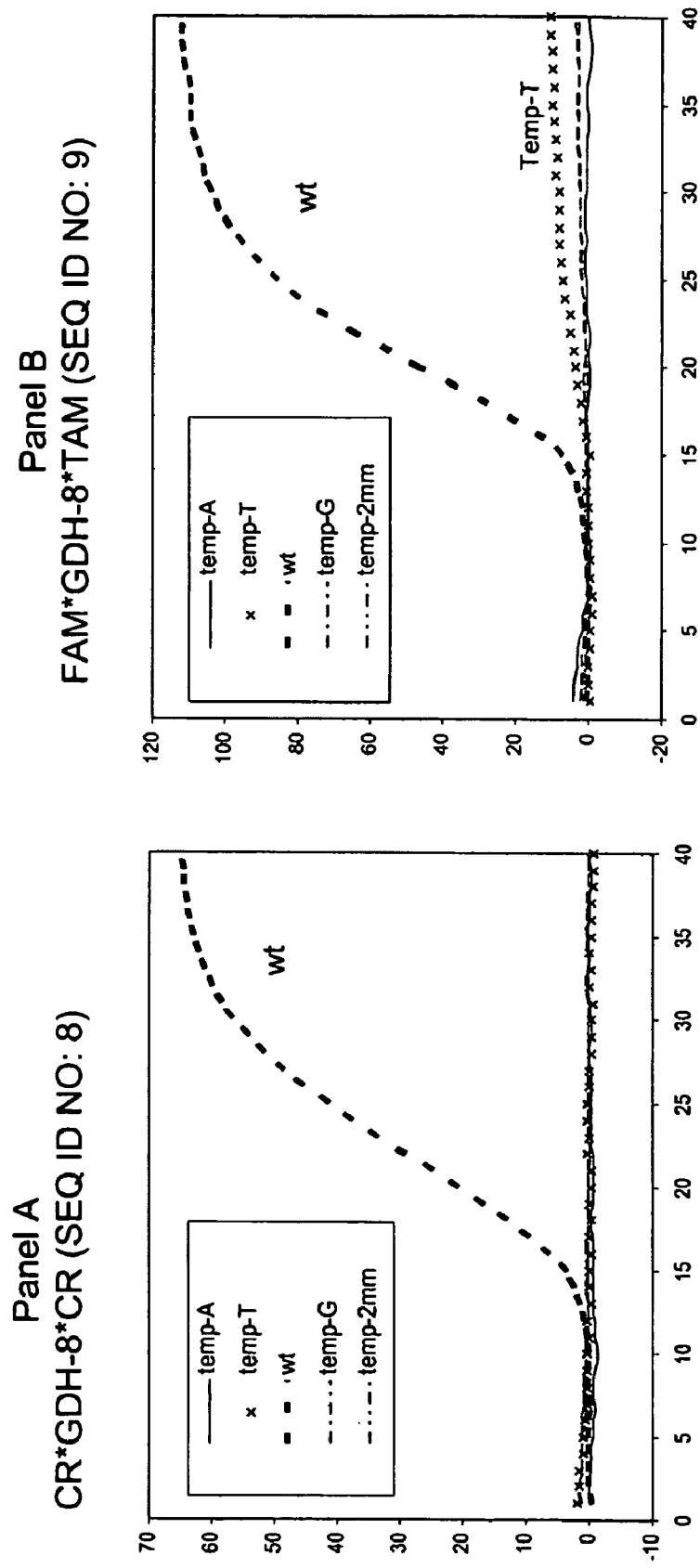

FIG. 6 depicts the results of a PCR reaction utilizing probes of the present invention that are capable of discriminating a single nucleotide mismatch. Panel A depicts the results utilizing probes designed according to the present invention. Panel B depicts the results utilizing conventional TaqMan® type probes of equivalent sequence.

Figure 7:
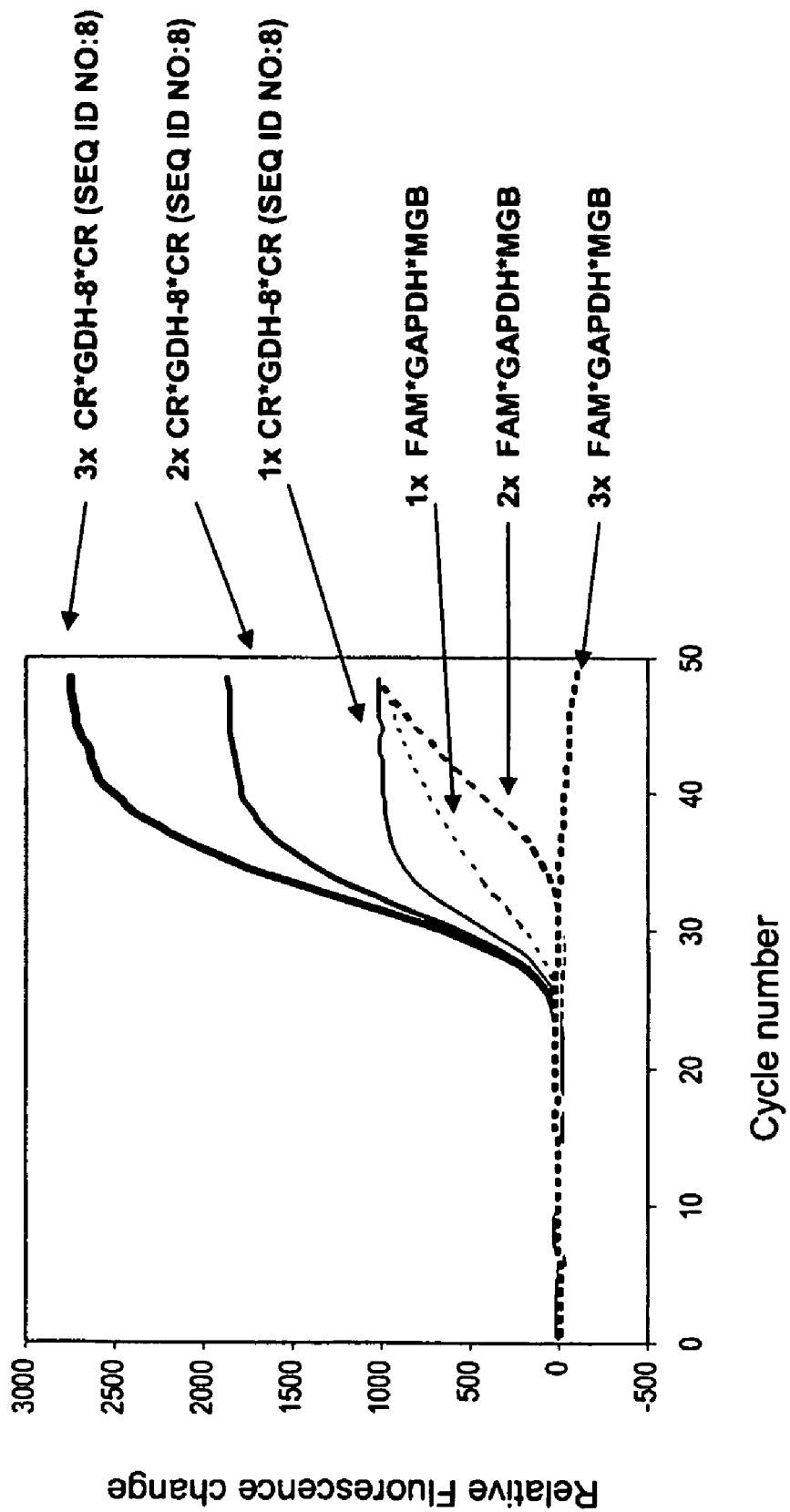

FIG. 7 is a graphical representation of the PCR signal intensity as a function of probe concentration in amplification experiments. The figure depicts the results generated by probes of the present invention and conventional TaqMan® type probes of equivalent sequence.

Figure 8:
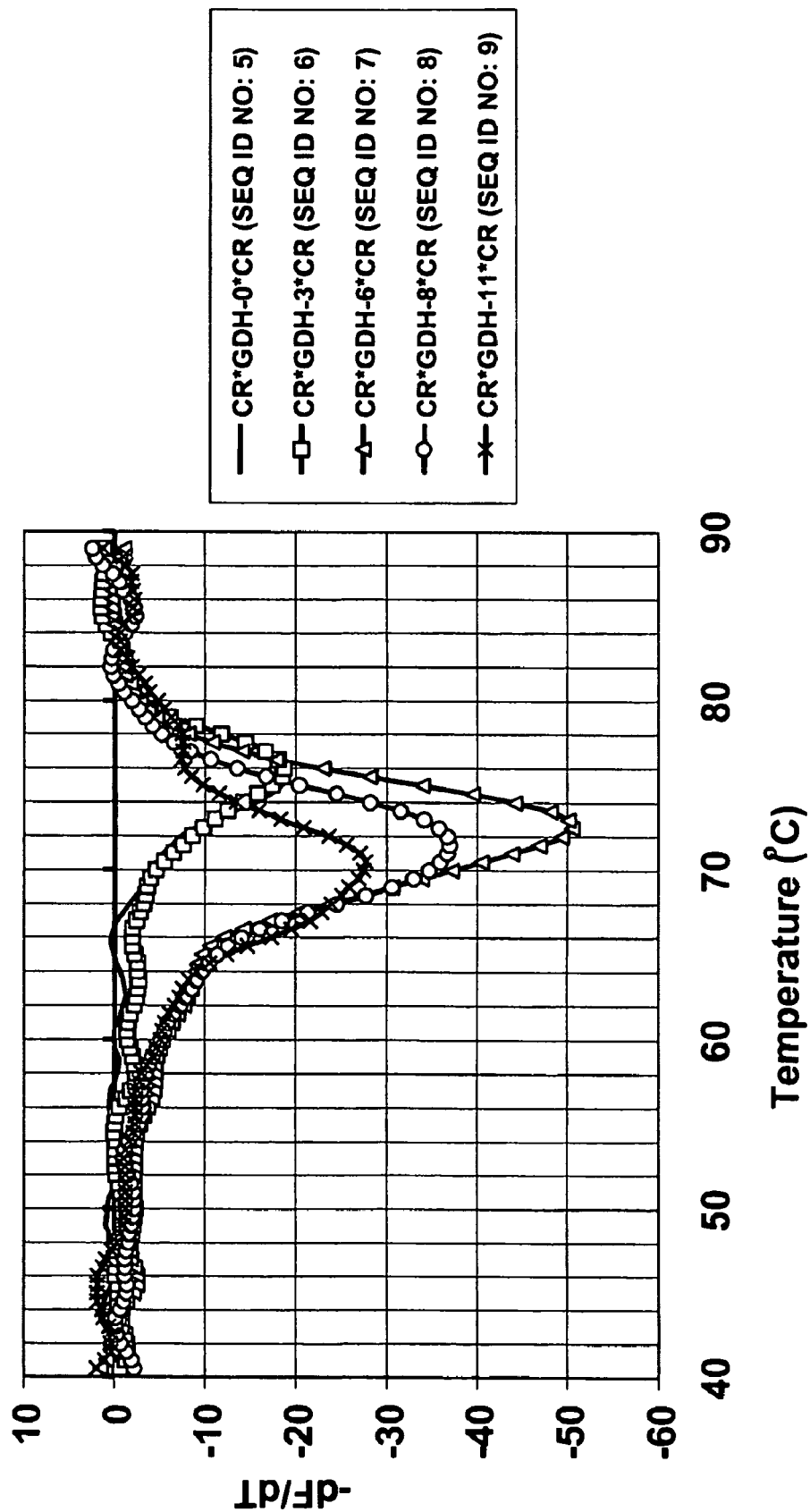

FIG. 8 shows the melting curves of hybrids formed between various dually 5-CR110-labeled GDH probes and their respective complements.

Figure 9:
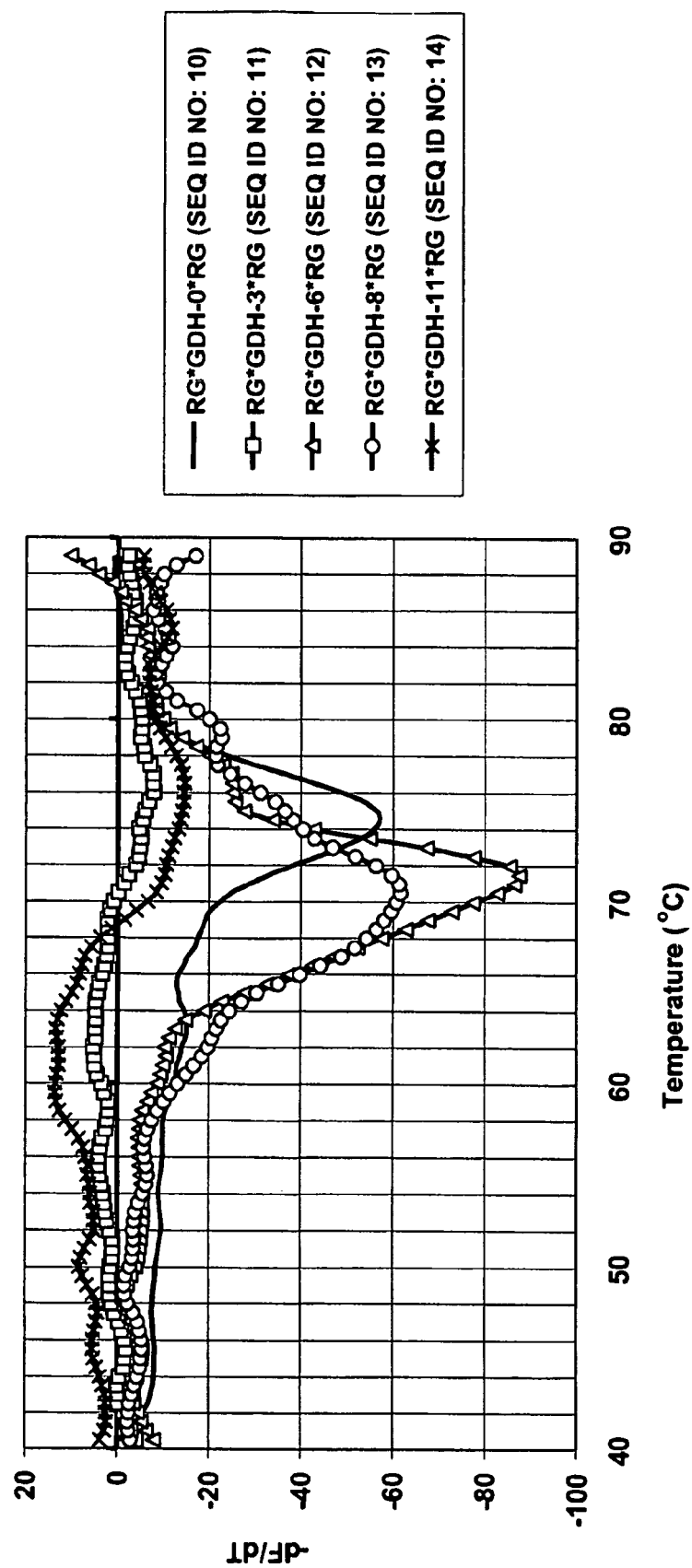

FIG. 9 shows the melting curves of hybrids formed between various dually 5-CR6G-labeled GDH probes and their respective complements.

Figure 10:
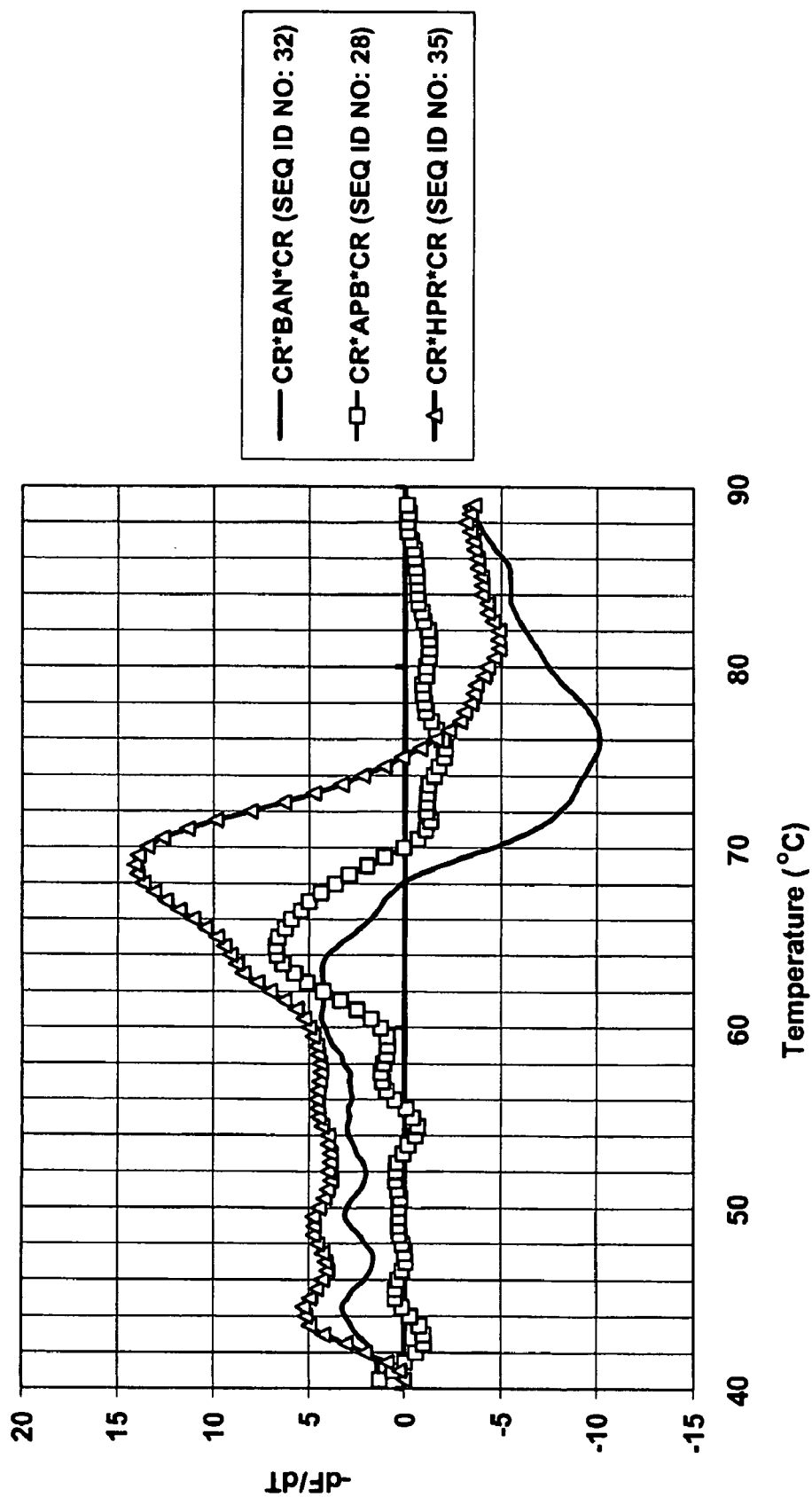

FIG. 10 shows the melting curves of three hybrids formed from three separate probes, dually 5-CR110-labeled BAN probe, dually 5-CR110-labeled APB probe and dually 5-CR110-labeled HPR probe, and their corresponding complements.

Figure 11:
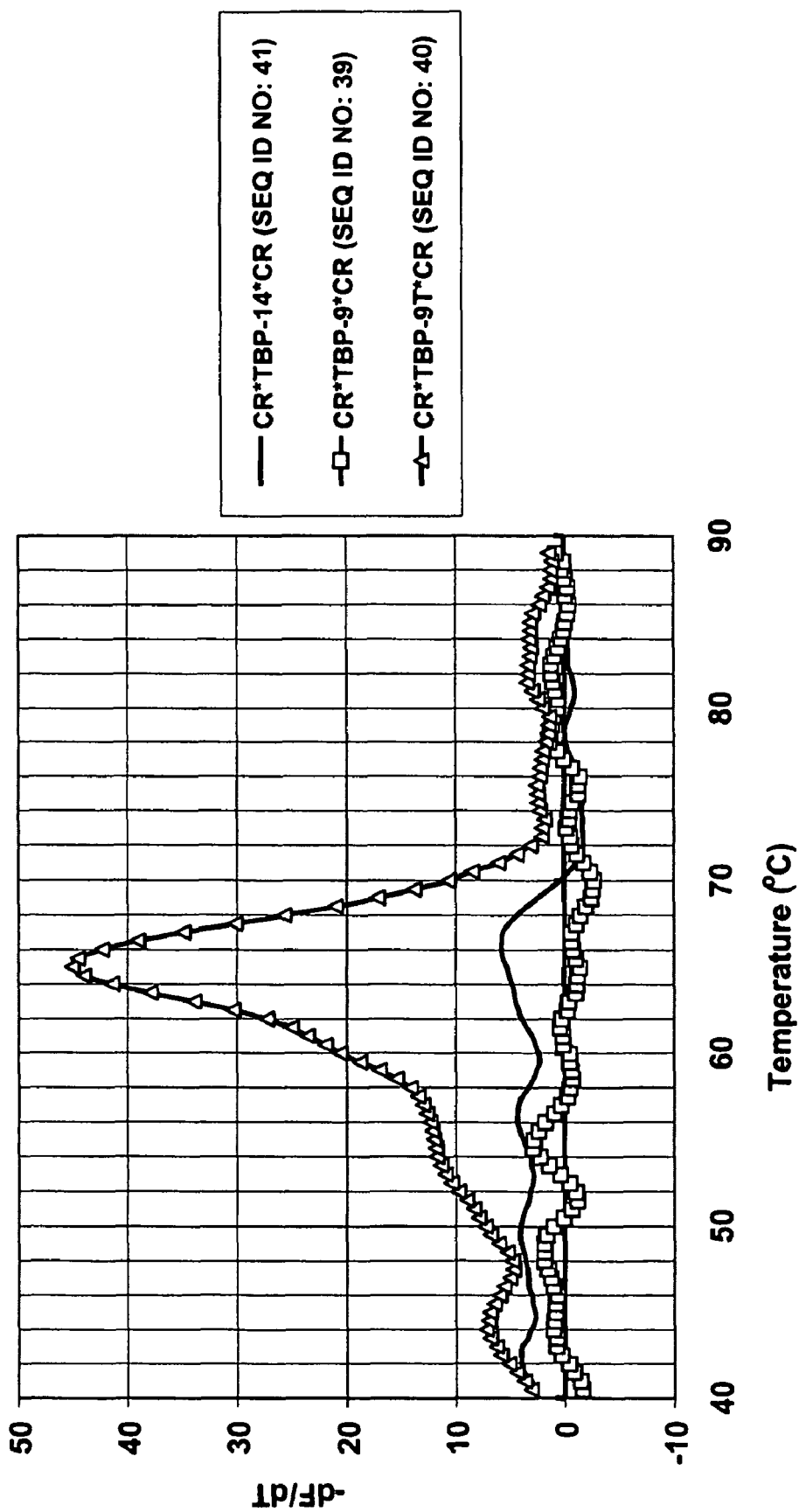

FIG. 11 shows the melting curves of hybrids formed between various dually 5-CR110-labeled TBP probes and their respective complements.

Figure 12:
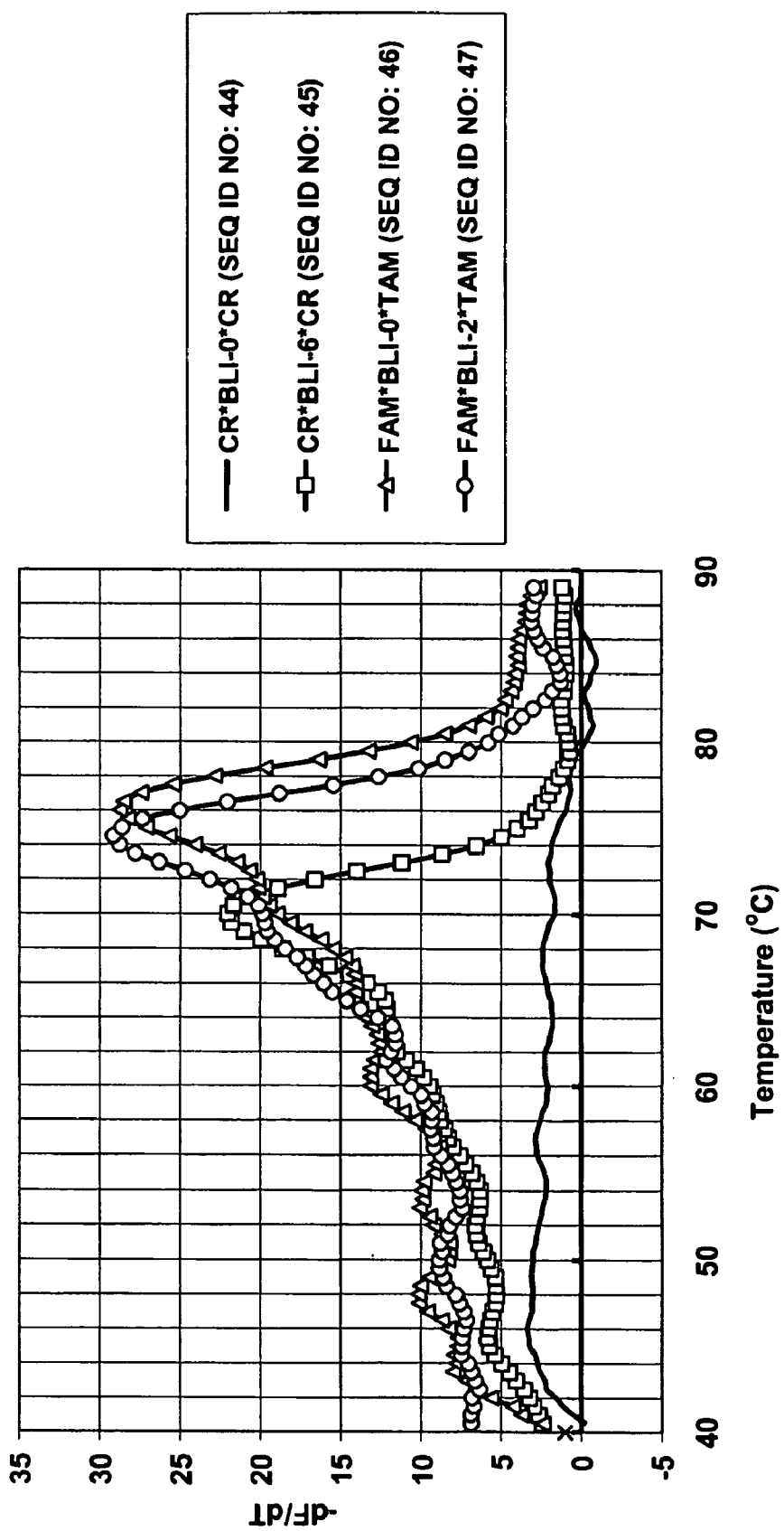

FIG. 12 shows the melting curves of two hybrids formed from two dually 5-CR110-labeled BLI probes and their respective complements, and two hybrids formed from two FAM/TAMARA-labeled TaqMan® probes and their respective complements.

TABLE 1 is a listing of probe sequences referenced herein as well as the structures of some of the exemplary linking molecules suitable for practicing the present invention.

TABLE 2 is a listing of reactive groups including some electrophilic and nucleophilic groups that can be utilized conjugating labeling molecules and quenching molecules to the probe sequences.

DETAILED DESCRIPTION OF THE INVENTION

While preferred embodiments of the present invention have been shown and described herein, it will be obvious to those skilled in the art that such embodiments are provided by way of Example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Definitions:

The terms "oligonucleotide" and "oligo" are used interchangeably and refer to a sequence of nucleic acids, 2'-deoxynucleic acids, peptide nucleic acids (PNA), locked nucleic acid (LNA) and other unnatural nucleic acids which include pyrazolo pyrimidine. In general oligonucleotides are of a length suitable for use as primers or probes. Most oligonucleotides are polynucleotides generally less than 100 nucleotides long, many are less than 50 nucleotides long and a number of oligonucleotides are comprised of 25 or fewer nucleotides.

"Primer" refers to an oligonucleotide that is capable of acting as a starting point to extend along a complementary strand. Primers usually are used as a set in PCR, one forward and one reverse. The forward primer contains a sequence complementary to a region of one strand of target nucleic acid and guides the synthesis along this strand. Similarly the reverse primer contains a sequence complementary to the opposite stand of the target nucleic and guides the synthesis along the opposite strand of target nucleic acid.

"Probe" refers to a labeled oligonucleotide containing a sequence complementary to a region of the target nucleic acid to effect detection of the target. Typically, the probe anneals to the target sequence downstream and generates a signal indicating the presence of the region of the target. In general, the signal is generated after hybridization, e.g., upon cleavage of the hybridized probe by the 5'-exonuclease activity of a polymerase that catalyzes the primer extension reaction. The probe can be blocked at the 3' terminus and is not extended into products.

The term 'reactive groups' refers to chemical moieties that may be useful in attaching various labeling groups including fluorophores and quenching molecules to oligonucleotides modified with functional groups capable of reacting with a label having the reactive group. It is understood that the term "reactive group" can be used to refer to a "reactive group" or a "functional group" and that the term "functional group" can be used to refer to a "reactive group" or a "functional group." Here, by way of convenience, but not limitation, a bond-forming group on a label will generally be referred to as a reactive group and a bond-forming group on an oligonucleotide will generally be referred to as a functional group. The bond formation reaction between a reactive group of, for example, a dye molecule and a functional group of an oligo is typically a reaction between a nucleophile and an electrophile. Accordingly, a reactive group can be either a nucleophile or a electrophile, and correspondingly a functional group can be either an electrophile or a nucleophile. A non-exhaustive list of pairs of electrophile/nucleophile can be found in Table 2.

Typical functional groups present on an oligo include, but are not limited to, amines, thiols, alcohols, phenols, aldehydes, ketones, hydrazines, hydroxylamines, disubstituted amines, halides, or carboxylic acids. More typical functional groups on an oligo are amines, thiols, alcohols, aldehydes or ketones. The most typical functional groups on an oligo are amines and thiols.

Common reactive groups attached to a dye molecules include, but are not limited to: acrylamide, an activated ester of a carboxylic acid, an acyl azide, an acyl nitrile, an aldehyde, an alkyl halide, an amine, an anhydride, an aniline, an arylhalide, an azide, an aziridine, a carboxylic acid, a haloacetamide, a halotriazine, a hydrazine, a hydrazide; an imido ester, an isocyanate, an isothiocyanate, a maleimide, a phosphoramidite, a sulfonyl halide or a thiol. Other reactive groups include succinimidyl ester, an amine, a haloacetamide, a hydrazine, an isothiocyanate, maleimide, or a phosphoramidite. When the functional groups present on the oligonucleotide are amines one commonly used reactive group on the dye used to attach the dye to the oligonucleotide is a succinimidyl ester or SE, in short.

Some of the abbreviations used for various fluorescent dyes are as follows: 5-CR110 refers to 5-carboxyrhodatnine110; 6-CR110 refers to 6-carboxyrhodamine110; 5-FAM refers to 5-carboxyfluorescein; 6-FAM refers to 6-carboxyfluorescein; 5-R6G refers to 5-carboxyrhodamine 6G; 5-ROX refers to 5-carboxy-X-rhodamine; 6-ROX refers to 6-carboxy-X-rhodamine; 5-TAMRA refers to 5-carboxytetramethylrhodamine; 6-TAMRA refers to 6-carboxytetramethyl-rhodamine; JOE refers to 2',7'-dimethoxy-4',5'-dichloro-6-carboxyfluorescein. To conjugate a dye from the above list to an amine-functionalized oligo, suitable carboxy group in the dye is first converted to an activated ester, preferably to a SE and then reacted with an amine on the oligo to form an amide bond linking the dye and the oligo. Thus, the indicated carboxy group in each of the above dyes is merely for conjugation purpose and will no longer be present following dye conjugation. In some instances of the following detailed description of the invention, a dye conjugated to an oligonucleotide may be referred to without mentioning the carboxy group of the dye used in the conjugation. In some other instances, the full name including the particular carboxy used for the conjugation of the dye may be used to indicate the particular isomer of the dye used in the conjugation.

The term "dye" refers to fluorescent or non-fluorescent molecules useful as labels of the probes of the present invention, which are distinct from the exemplified conventional TaqMan® robes and 1,2 dihydro [3,2c]indole (CDPI) containing and pentameric N-methylpyrrole-4-carbox-2-amide ($MPC_5$) containing MGB probes. An exemplary dye may adopt an aromatic structure and can comprise one or more of the following structural moieties generalized based on numerous aromatic structures provided herein:

Moiety a: $Ar^1$
Moiety b: $Ar^2$-$(L)_n$-$Ar^3$
Moiety c: $Ar^4$—N=N—$Ar^5$ wherein each of moieties a, b and c typically has at least one absorption peak with a wavelength $\geq 340$ nm but typically less than 800 nm, and can be between 400 nm to 700 nm; $Ar^1$ is a substituted or unsubstituted fused aryl system comprising at least two 6-membered rings and optionally at least one heteroatoms selected from O, N, and S; each of $Ar^2$, $Ar^3$, $Ar^4$, and $Ar^5$ is a substituted or unsubstituted aryl or fused aryl ring optionally comprising at least one heteroatom selected from O, N and S; L is a substituted or unsubstituted methine group; and n is an integer selected from 1-7.

A dye can be spectrally similar. A spectrally similar dye may or may not have similar chemical structures but possess similar excitation and/or excitation spectral properties. The emission spectra of the dyes, however, may or may not be similar. An example of one such pair is 5-FAM and 5-CR110. 5-FAM has absorption/emission wavelengths at 495/519 nm while 5-CR110 has absorption/emission at 502/524 nm. For the purpose of the present invention, absorption or excitation wavelengths having a difference within 15 nm are considered to be similar. A dye can be spectrally identical. A spectrally identical dye may or may not have the same chemical structures but have either emission profiles or excitation or both emission and excitation profiles that are spectrally indistinguishable.

The term "same dyes" refers to fluorescent dyes that are chemically identical. However, two of the same chemical entity when conjugated to a probe may perform different functions with respect to each other. For example; one of the same molecules (e.g., conjugated to the 5' end of the probe) may act as a reporter dye whose fluorescence contributes to the signal detected after the probe is hybridized to a target nucleic acid. The other dye having the same structure (e.g., conjugated to the 3' end of the probe) may act as a quencher dye with respect to the first dye as it reduces the signal of the first dye when the probe is not hybridized with the target nucleic acid.

The term "reporter dye" or "fluorescent reporter dye" refers to a fluorescent dye whose fluorescence contributes to the detected fluorescence signal during an assay, which signal if desired, can be monitored during the assay.

As used herein, the terms "quench" or "quenches" or "quenching" or "quenched" refer to reducing the signal produced by a molecule, it includes, but is not limited to, reducing the signal produced to zero or to below a detectable limit. Hence, a given molecule can be "quenched" by, for example, another molecule and still produce a detectable signal albeit the intensity of the signal produced by the quenched molecule will be smaller when the molecule is quenched than when the molecule is not quenched.

The term "quencher" or "quencher molecule" refers to a dye or an equivalent molecule, such as nucleoside guanosine (G) or 2'-deoxyguanosine (dG), which is capable of reducing the fluorescence of a fluorescent reporter dye or donor dye. A "quencher dye" refers to a dye molecule capable of quenching the fluorescence of another dye. A quencher dye may be a fluorescent dye or non-fluorescent dye. When the quencher dye is a fluorescent dye, its fluorescence wavelength can be substantially different from that of the reporter dye and the quencher fluorescence is usually, but not always, not monitored during an assay. The quencher dye can have the same chemical structure as the reporter dye, though when used as in pairs, one quenches signals from the other one of the same pair. In some instances, a pair of reporter and quencher function via the action of FRET or other non-FRET mechanisms.

As used herein, the terms "dequench" or "unquench", "dequenching" or "unquenching", "dequenched" or "unquenched" are antonyms to the terms "quench", "quenching" and "quenched", respectively, as defined above herein.

The term "random conformation" refers to a range of undefined possible secondary structures of an unhybridized oligonucleotide at any given time as a result of free intramolecular rotation and vibration. An oligonucleotide of random conformation according to the invention generally does not form a hairpin structure.

The term "melting temperature" or "$T_m$" of an oligonucleotide is defined as the temperature at which 50% of the limiting strand of a complementary pair are in hybridized form and 50% are in unhybridized form under a given ionic strength and pH condition. The melting temperature of an unlabeled oligonucleotide may be calculated using any of the several known computer software programs. A calculated melting temperature, vary somewhat, depending on which software is used in the calculation. Calculated temperatures are often used as a guide in designing probes and primers to ensure proper hybridizations of the probes and primers. Throughout the disclosure, the calculated melting temperature of an oligonucleotide refers to a temperature calculated according to the method of SantaLucia (PNAS 95, 1460-1465, 1998), assuming a salt concentration of 60 mM and an oligonucleotide concentration of 500 nM.

Design of the Probes of the Present Invention:

One aspect of the present invention relates to the design of dually labeled oligonucleotide probes ("DOPs"). The subject designs are particularly useful for high-sensitive nucleic acid detections via hybridization assays including but not limited to template-directed amplification reactions. The DOPs of the present invention exhibit one or more following features.

The subject probes for a target nucleic acid generally comprise complementary sequences that are shorter than those of the conventional probes such as TaqMan® probes. A typical TaqMan® probe has a calculated melting temperature of about 70° C., and has a length of about 32 to about 35 nucleotides (Keohler R T and Peyret N, Comput Biol. Chem. 2005 29(6):393-7; Keohler R T and Peyret N 2005 Bioinformatics 21(16):3333-9). A probe of the present invention may, if desired, made to be 40% shorter than an average TaqMan® probe. However, the performance of the subject probes is comparable and often superior to that of the conventional designs. The subject probes are generally easier to manufacture. The yield of production is generally higher because, in part, the nucleotide sequences to be synthesized are typically shorter. In addition, the chemistry required for the synthesis of the subject probes is generally simpler than that required for conventional probes such as CDPI-containing MGB probes or pentamer of N-methylpyrrole-4-carbox-2-amide ($MPC_5$) containing MGB probes. Furthermore, the subject probes exhibit less inhibition effect as compared to a conventional TaqMan® MGB probes on a template-directed polymerization process including end-point PCR, real-time PCR and single nucleotide polymorphism detection.

In one embodiment, a subject DOP comprises a first dye that is fluorescent and a second dye that are separated by at least about 5 nucleotide bases, wherein the two dyes are configured in a manner such that the first dye acts as a reporter that contributes to a fluorescent signal detected after hybridization of the probe with a target nucleic acid, and the second dye acts as a quencher of the first label; and wherein at least one of the two dyes (or both) enhances probe hybridization such that the probe has a calculated melting temperature (calculated Tm) that is no more than 5° C. higher than that of a primer used in conjunction with the probe in amplifying the target sequence in an amplification reaction. In one aspect, the probe has a calculated melting temperature (calculated Tm) that is within ±5° C., or ±4° C., ±3° C., ±2° C., or ±1° C., inclusive, of a primer used in conjunction with the probe in amplifying the target. In another aspect, the probe has a calculated Tm no more than about 4° C., 3° C., 2° C., or 1° C. higher than that of a primer used in conjunction with the probe in amplifying the target. In yet another aspect, the probe has a calculated melting temperature (calculated Tm) that is substantially the same or lower (e.g., −25° C., −20° C., −15° C., −10° C., −9° C., −8° C., −7° C., −6° C., −5° C., −4° C., −3° C., −2° C. or −1° C.) as compared to that of a primer used in conjunction with the probe in amplifying the target sequence. Where desired, both of the first and the second dye are fluorescent.

The primer used in conjunction with the probe in amplifying the target sequence typically hybridizes to a different region of the target, generally upstream (to the 5' end) of the probe. The primer hybridizes to the same strand of the target nucleic acid to which the probe hybridizes. In some context, this reference primer is termed a "related primer." Conversely, the other primer of the primer pair that hybridizes to the complementary strand of the same target nucleic acid is the "unrelated primer". The reference or related primer can comprise any sequence of the target nucleic acid which demarks the beginning of the replica strand. The calculated Tm of a particular primer refers to the annealing temperature of the primer, which can fall within a wide range of temperatures. Any primer having a calculated Tm within the range of about 45° C. to 70° C., preferably about 55° C. to 68° C., preferably about 55° C. to 65° C. can be used as a reference primer in designing the probes of the present invention.

The calculated melting temperature of the probe (Tm) refers to the theoretically calculated melting temperature of an oligonucleotide that has not been conjugated with any moieties. Such calculated temperature is usually an estimate of the actual melting temperature of an oligonucleotide and is based on the sequence of the oligonucleotide without considering the effect of any labels and any associated linkers. Given the exact sequence of an oligonucleotide, the melting temperature of the oligonucleotide can be readily predicted or calculated using any of the widely available software programs, such as those described by Panjkovich, et al. (Panjkovich, et al. *Nucleic Acids Res.* 33:570-572 (2005)), Owczarzy, et al. (Owczarzy, et al. *Biochemistry* 43:3537-3554 (2004)), and SantaLucia (PNAS 95:1460-1465 (1998)), and commercial software programs used for probe and primer designs, such as Primer Express from Applied Biosystems (Foster City, Calif.). The melting temperature calculated in this manner may vary somewhat from software to software. Throughout the present disclosure, the melting temperature of an oligonucleotide is calculated using the method of SantaLucia (Proc. Natl. Acad. Sci. vol 95, pp 1460-1465, 1998), assuming a salt concentration of 60 mM and an oligonucleotide concentration of 500 nM. The Tm of the probe is defined relative to the Tm of the related primer. Regardless of the choice of the particular software programs or methodologies, the same software program or methodology is used to ascertain the calculated melting temperature of the related primer and the probe of the present invention.

For example, if the melting temperature of a primer is 58° C.-60° C., as recommended in PE Biosystem Primer Express Technical Manual (Applied Biosystems, Inc. Foster City, Calif.), the temperature range of a subject probe having "$T_m \pm 5°$ C." would be equivalent to a range of from about 53° C. to about 65° C. Similarly, the temperature range defined by "$T_m \pm 4°$ C." would be equivalent to a range of from about 54° C. to about 64° C. It is readily understood to one skilled in the art that the optimal melting temperature for a primer will depend on the annealing/extension temperature used in a PCR protocol. In general, the melting temperature of a primer should be chosen to be around the annealing/extension temperature used in the PCR protocol. For example, if an annealing/extension temperature of 50° C. is used in a PCR protocol, a primer melting temperature of around 50° C. many be selected, and accordingly the probe of the appropriate calculated melting temperature can be selected according to the perimeters defined herein.

In a related but separate embodiment, the present invention also provides a dually labeled oligonucleotide probe comprising less than 15 nucleotides that hybridizes to a region in a target sequence. The probe typically comprises a first dye that is fluorescent and a second dye, the two dyes being configured in a manner such that the first fluorescent dye acts as a reporter that contributes to a fluorescent signal detected after hybridization of the probe with the target nucleic acid, and the second dye acts as a quencher of the first dye; and wherein at least one of the two dyes enhances probe hybridization such that the probe exhibits an observed melting temperature (observed Tm) that is higher than that of a corresponding probe lacking the at least one of the two dyes. Where desired, the observed Tm is at least about 1° C., 2° C., 3° C., 4° C., 5° C., 6° C., 7° C., 8° C., 9° C., 10° C., 15° C., 20° C. or 25° C. higher than that of a corresponding probe lacking the at least one of the two fluorescent dyes.

Methods of measuring DNA or oligonucleotide melting temperatures to derive the observed Tm are available in the art. When a double-stranded DNA (probe/target hybrid) is heated up to melt, the fluorescence changes as a result of dye dissociation from the dsDNA. The temperature corresponding to the inflection point of the fluorescence intensity (F) vs. temperature (T) plot, or the temperature corresponding to the peak of the −dF/dT vs T plot, is the measured melting temperature of the probe. As another example, the observed melting temperature of a subject probe may be measured by absorption spectrum. When a probe/target hybrid is heated, the absorbance at 260 nm increases as a result of dissociation of the dsDNA into ssDNA. The temperature corresponding to the half maximal absorbance at 260 nm is the melting temperature of the probe. Various methods of measuring probe melting temperature may yield different results, even for the same probe. For example, the melting temperature obtained using an intercalating dye may be generally higher than that obtained using the UV absorption method because the dye may have an effect of stabilizing the DNA duplex structure. Also, depending on the nature and the concentration of the intercalating dye used, the measured melting temperature may differ. In addition, the concentration of the complementary strand in forming the duplex for the test will also likely affect the measured melting temperature. Nevertheless, for the purpose of the present invention, as long as the melting temperatures for both the related primer and the probe are measured using the same method under the same condition, the melting temperature relation between the probe and the related primer should stay relatively constant and thus would normalize any discrepancies contributed by other facts, if present. Similarly, the suitability of the at least one CEPH dye can be readily determined by preparing a probe comprising said at least one dye and comparing the melting temperature of said probe and the melting temperature of the related primer under the same condition.

The attainment of such a sufficiently high melting temperature is due to, in part, the unique property of at least one of the two labels attached to the probe. In one embodiment, at least one of the two labels attached to the probe must be a dye capable of enhancing probe hybridization (hereinafter "CEPH dye"). One of the two dyes acts as a reporter dye and the other dye acts as a quencher. The reporter and the quencher dyes are defined in functional terms, such that these dyes can be of the same or different chemical structures, albeit serving, relative to each other, a different function when used in a hybridization reaction. A reporter dye contributes to a fluorescent signal detected after hybridization of the probe with a target nucleic acid, whereas the other dye acts as a quencher of the first dye. A net increase in reporter signal after hybridization may result from one or more mechanisms separately or simultaneously. An increase in signal can be effected by way of spatial extension or separation of the reporter dye from the quencher dye while both are still attached to the probe. In addition, either the reporter or the quencher dye of the probe can be separated by way of cleavage via an enzyme (e.g., a polymerase having a 5' to 3' exonuclease activity), thereby generating a reporter signal that is detected. Some of the subject reporter dyes contribute to the signal detected as soon as it hybridizes with the target sequence and others do so only when the reporter is physically separated from the quencher via the action of an enzyme (e.g., by either cleavage of the reporter or the quencher from the probe). Some reporter dyes do not contribute substantially a signals detected. Some reporter dyes of the latter group may exhibit a reduction in signal at the moment of hybridizing with the target nucleic acid. So long as it contributes to the signal detected at any point after the hybridization (including the moment when the probe just form a stable complex with the target nucleic acid sequence), it can be a considered as a reporter dye in the context of the subject probes.

As used herein, a dye molecule attached to a probe is a quencher if it reduces the emission of an optical signal when the probe is not hybridized with the target nucleic acid (typically when the probe assumes a random state). The same dye molecule can become a reporter dye upon being cleaved by an enzyme after hybridization with the target nucleic acid as the signal of the dye is now detected during the assay. In some instances, the quencher dye can be non-fluorescent and it functions primarily to suppress the signal of the reporter dye when the probe is not hybridized with the target sequence.

Where desired, either the reporter or the quencher dye or both can exhibit the capability to enhance probe hybridization. Such capability can be ascertained in a variety of ways. In one aspect, the capability is met if the CEPH dye increases the melting temperature of the probe via physical attractive interactions between the CEPH dye and a target DNA. Such attractive interactions may include electrostatic interaction, hydrophobic interaction and hydrogen bonding. As a DNA molecule is highly negatively charged, a CEPH dye generally does not bear a net negative charge, as such a charge may cause repulsive interaction between the dye and the target DNA, destabilizing the hybridization of said probe. In general, a CEPH dye is a positively charged dye, or a dye of neutral charge. A CEPH dye of neutral charge can be a dye bearing no charged groups within the dye molecule, or a zwitterionic dye bearing a positive charge and a negative charge.

A vast diversity of fluorophores are suitable for use as the dyes of the subject probes. They include but are not limited to 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, BODIPY™ and its derivatives and analogs, Brilliant Yellow, cyanine dyes such as Cy3 and Cy5 and other derivatives, coumarin and derivatives such as coumarin, 7-amino-4-methylcoumarin (AMC, Coumarin 120), 7-amino-4-trifluoromethylcoumarin (Coumarin 151), 4',6-diaminidino-2-phenylindole (DAPI), isothiocyanatophenyl)-4-methylcoumarin, 5-[dimethylamino]naphthalene-1-sulfonyl chloride (DNS, dansyl chloride), ethidium, fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; 4-methylumbelliferone; oxazine dyes such as Nile Blue and other analogs; pyrene and derivatives such as pyrene, pyrene butyrate and succinimidyl 1-pyrene butyrate; rosamine dyes, tetramethyl rosamine, and other analogs, rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA), tetramethyl rhodamine; tetramethyl rhodamine isothiocyanate (TRITC), and thiazine dyes such as methylene blue and analogs. Additional fluorophores applicable for use in the present are disclosed in U.S. Pat. No. 5,866,366 and WO 01/16375, both of which are incorporated herein by reference. Additional examples are described in U.S. Pat. No. 6,399,335, published U.S. patent application No. 2003/0124576, and The Handbook—A Guide to Fluorescent Probes and Labeling Technologies, Tenth Edition (2005) (available from Invitrogen, Inc./Molecular Probes), all of which are incorporated herein by reference.

Further, in some of the embodiments of the invention, non-fluorescent labels may be used in the probes of the invention. Numerous non-fluorescent quenchers have been developed and are commercially available, such as the azo dye-based Black Hole Quencher (BHQ) from BioSearch, Inc., polynitro cyanine dyes from Amersham, Inc. and the rhodamine-based QSY dyes from Molecular Probes, Inc.

Non-limiting examples of preferred CEPH dye include a rhodamine dye, a positively charged cyanine dye, a rosamine dye, a Black Hole quencher dye, Malachite Green, an oxazine dye, and a thiazine dye.

In one aspect, a reporter CEPH dye can be a positively charged reporter dye having a delocalized positive charge or a zwitterionic reporter dye having a delocalized positive charge and a negative charge. In a separate aspect, a quencher CEPH dye is a quencher dye selected from the group consisting of a positively charged quencher having a delocalized positive charge, a zwitterionic quencher having a delocalized positive charge and a negative charge, a neutral or positively charged quencher having an azo moiety. Examples of reporter or quencher CEPH dyes having a delocalized positive charge include, but are not limited to, positively charged cyanine dyes and rosamine dyes. Examples of zwitterionic reporter or quencher CEPH dyes include, but are not limited to, rhodamine dyes. Examples of neutral quencher CEPH dyes include, but are not limited to, neutral azo dyes, such as the Black Hole quencher dyes. Azo dyes are dyes that contain an azo moiety, —N=N—, which typically renders a dye non-fluorescent, therefore is a suitable quencher dye.

Preferred rhodamine dyes have the following general structure of structural Formula 1:

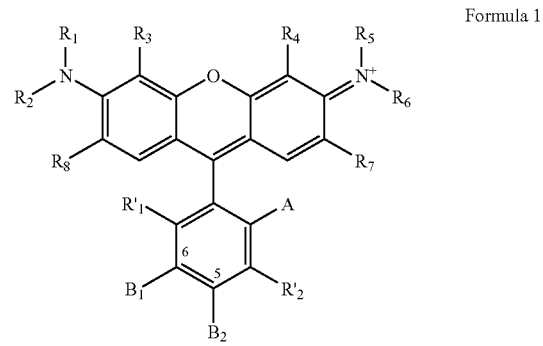

Formula 1 wherein $R_1$-$R_8$ are H or C1-C3 alkyls, where each pair of $R_1$ and $R_2$, $R_2$ and $R_8$, $R_1$ and $R_3$, $R_4$ and $R_5$, $R_5$ and $R_6$, and $R_6$ and $R_7$, optionally and independently forms a 5- or 6-membered ring, which may optionally comprise up to one double bond and/or one or more C1-C2 alkyl substituents; A is —$CO_2^-$ or —$SO_3^-$; $R'_1$ and $R'_2$ are each independently H, F or Cl; one of $B_1$ and $B_2$ represents the attachment site of said oligonucleotide, and the reminder of $B_1$ and $B_2$ is H, F or Cl. More specifically preferred rhodamine dyes include carboxy-rhodamine 110, carboxy-rhodamine 6G, carboxy-tetramethylrhodamine (TAMRA), ROX and Texas Red. Most of the rhodamine dyes typically have two isomeric forms, 5- and 6-carboxy isomers. Preferably, a single isomer, either 5-carboxy isomer or 6-carboxy isomer, is used for the labeling. Most rhodamine dyes are fluorescent and thus can serve as reporter CEPH dyes. Rhodamine dyes can also serve as quencher CEPH dyes when paired with a suitable reporter dye using the guideline described herein. Some rhodamine dyes are non-fluorescent. For example, the quencher dye, QSY7 (Molecular Probes, Eugene, Oreg.), is nonfluorescent. Non-fluorescent rhodamine dyes can serve as quencher CEPH dyes of the probes of the present invention.

Preferred positively charged cyanine dyes have the following general structure of structural Formula 2:

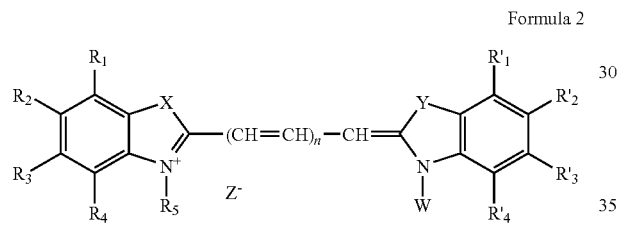

Formula 2 wherein each of R1-R4 and R'1-R'4 is independent selected from H, C1-C4 alkyl, F, Cl and Br; alternatively, each pair of $R_1$ and $R_2$ in combination and $R'_1$ and $R'_2$ in combination independently form a fused benzene ring; $R_5$ is a C1-C3 alkyl; X and Y are independently selected from $C(CH_3)_2$, O, S and $NR_6$, where $R_6$ is a C1-C2 alkyl; n is selected from 1, 2 and 3; W represents the attachment site of said oligonucleotide; and E is an anion for balancing the positive charge of the dye.

The probe of the invention may comprise the dual labels in various combinations of dye functions and attachment sites. In general, the dye pair may either be a reporter-reporter pair or a reporter-quencher pair, wherein at least one of the labels in each pair is a CEPH dye. In general, one of the labels is on the 5'-side of the oligonucleotide and the other label on the 3'-side of the oligonucleotide. Preferably, the at least one reporter dye is on the 5'-side of the oligonucleotide and the quencher CEPH dye is on the 3'-side of the oligonucleotide. Preferably, the two labels are separated from one another by at least 5, 8, 9, 10, 11, 12, 13, 14, 15, 20 or more nucleotides. In one embodiment of the invention, said probe comprises a reporter dye attached at the 5'-terminus and a quencher dye attached at the 3'-terminus, wherein the reporter dye is an overall negatively charged fluorescent dye selected from the group consisting of fluorescein, a fluorescein derivative, a Alexa Fluor dye and a Cy dye; the quencher dye is a CEPH dye selected from the group consisting of a rhodamine dye of Formula 1, a QSY dye, a positively charged cyanine dye of Formula 2, and a Black Hole quencher. Various fluorescein derivatives are commercially available from Applied Biosystems, Inc. (Foster City, Calif.) or Molecular Probes, Inc. (Eugene, Oreg.), and have the commercial names of JOE, HEX, NED, TET, Oregon Green, for example.

In one more preferred embodiment of the invention, said probe comprises a first reporter CEPH dye attached at the 5'-terminus and a second CEPH dye attached at the 3'-terminus that reduces the signal of the first reporter dye when the probe is not hybridized with the target sequence. In a preferred embodiment of the invention, the first CEPH dye and the second CEPH dye are the same dye which quenches the signal of each other prior to hybridization of the probe with the target sequence and contributes to the signal detected after hybridization. The same dye can be selected from the group consisting of rhodamine dyes of Formula 1 and positively charged cyanine dyes of Formula 2.

Shown below are additional dyes that can be incorporated into the probes of the present invention.

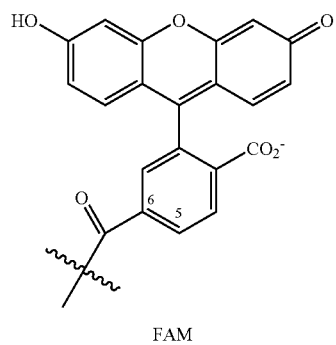

FAM

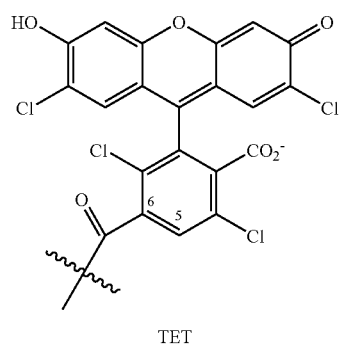

TET

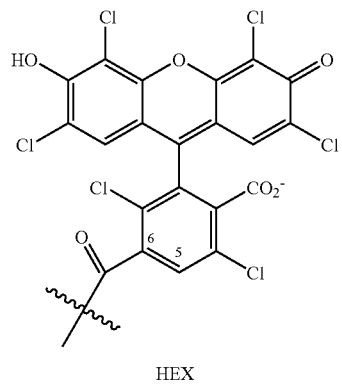

HEX

-continued
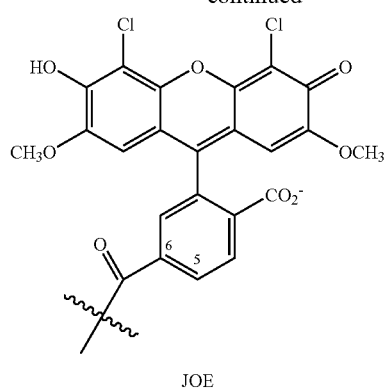
JOE
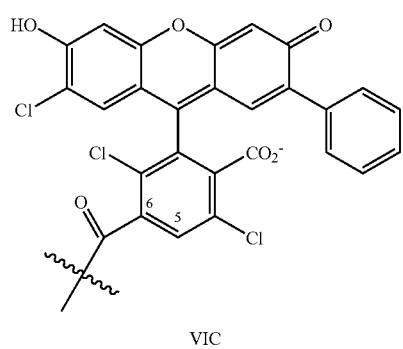
VIC
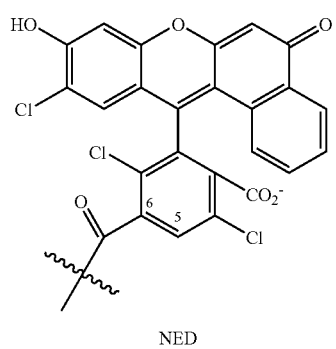
NED
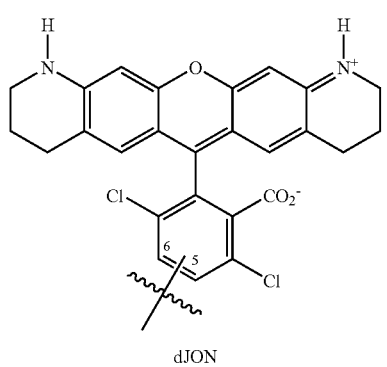
dJON
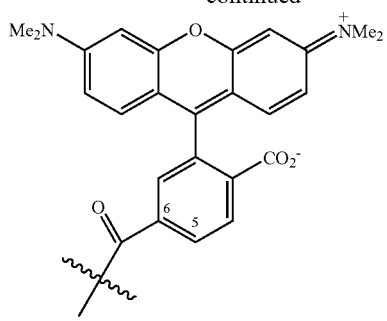
TAMRA
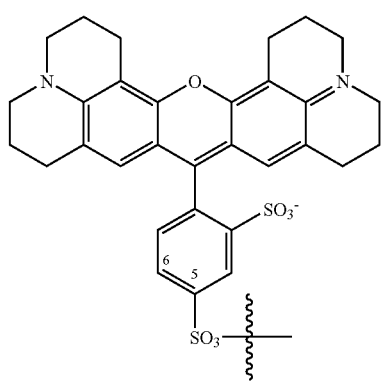
Texas Red
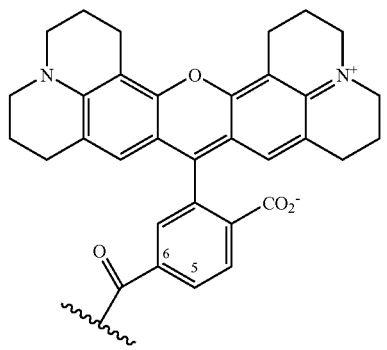
ROX
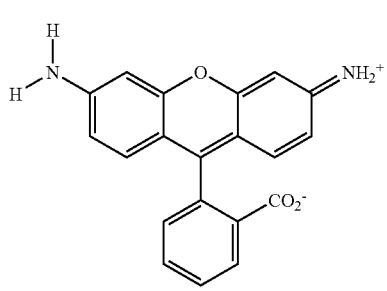
Rhodamine 110

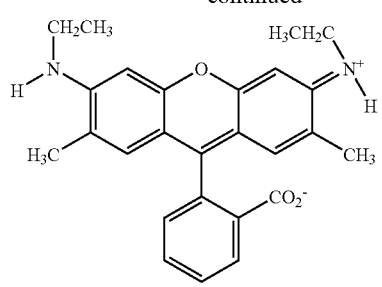
Rhodamine 6G
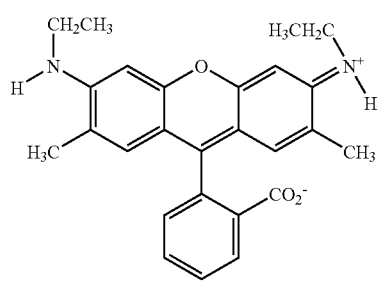
Rhodamine 6G
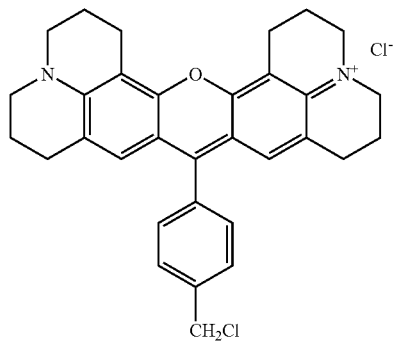
MitoTracker® Red CMXRos
(rosamine dye)
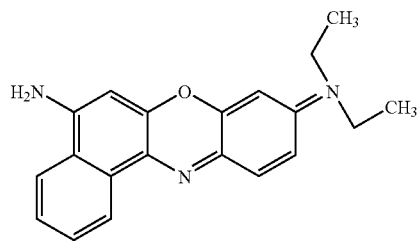
Nile blue
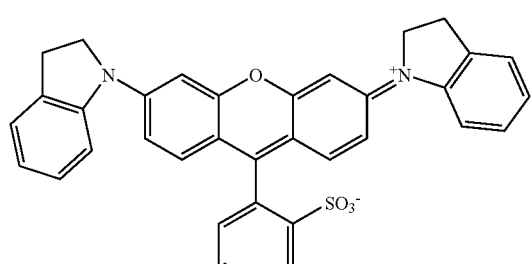
QSY 21
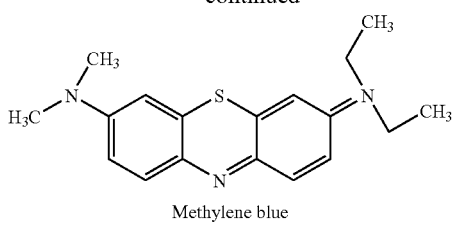
Methylene blue
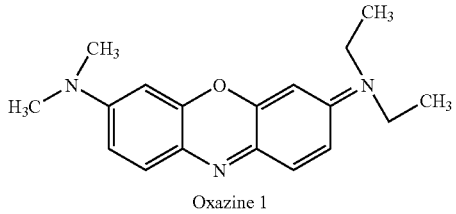
Oxazine 1
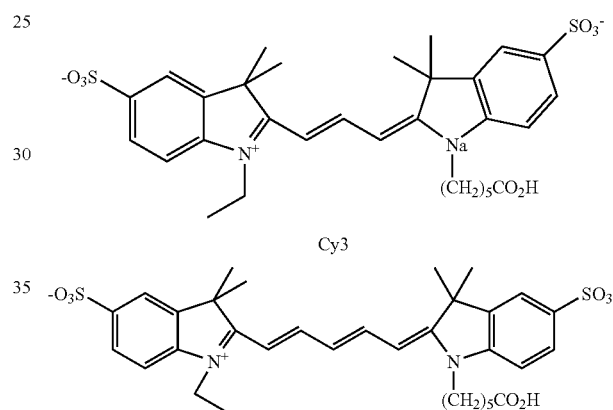
Cy3
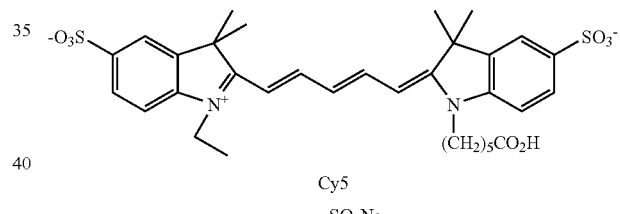
Cy5
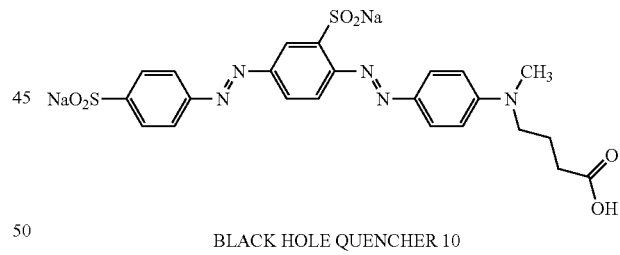
BLACK HOLE QUENCHER 10
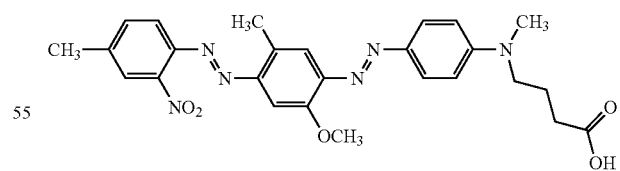
BLACK HOLE QUENCHER 1
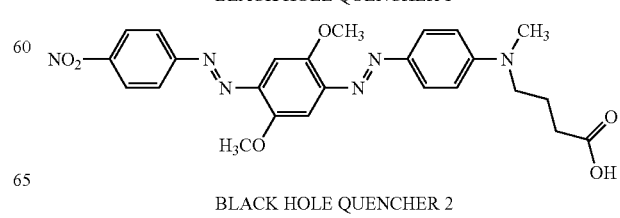
BLACK HOLE QUENCHER 2

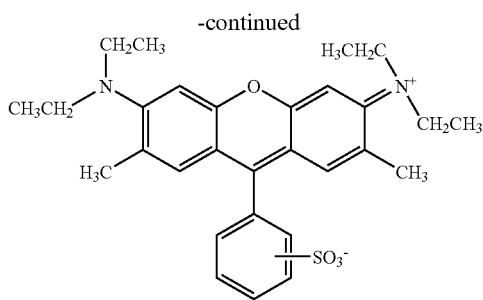
Lissamine

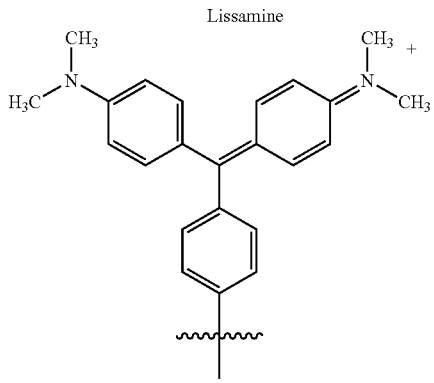
MALACHITE GREEN

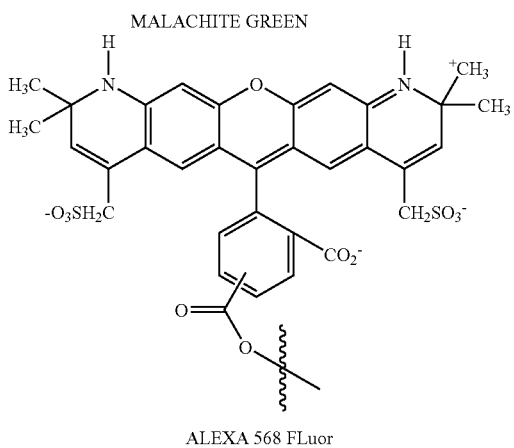
ALEXA 568 FLuor

Preparation of the Probes of the Present Invention:

The present invention provides a method of preparing the probes described in the present invention. Accordingly, in one embodiment, the method comprises: a) selecting a nucleotide sequence complementary to a region of the target; b) selecting at least two fluorescent dyes separated by at least 5 nucleotides to said nucleotide sequence, wherein the two dyes are configured such that the first dye acts as a reporter contributing to a fluorescent signal detected after hybridization of the probe with a target nucleic acid, and the second label acts as a quencher of the first label when the probe is not hybridized with the target nucleic acid; and wherein at least one of the two labels enhances probe hybridization such that the probe has a calculated melting temperature that is no more than 5° C. higher than that of a primer used in conjunction with the probe in amplifying the target sequence in an amplification reaction; and c) synthesizing the probe based on the selected nucleotide sequence and the selected dyes.

In a related embodiment, the method of preparing a dually labeled probe specific for a nucleic acid target, comprising: a) selecting a nucleotide sequence complementary to a region of the target, said nucleotide sequence comprising less than 15 nucleotide bases; b) selecting at least two fluorescent dyes being configured in a manner such that the first fluorescent dye acts as a reporter contributing to a fluorescent signal detected after hybridization of the probe with the target nucleic acid, and the second dye acts as a quencher of the first dye; and wherein at least one of the two dyes enhances probe hybridization such that the probe exhibits an observed melting temperature (observed Tm) that is higher than that of a corresponding probe lacking the at least one of the two dyes; and c) synthesizing the probe based on the selected nucleotide sequence and the selected dyes.

Any of the aforementioned methods can be performed with the aid of a computer, or a computer-assisted program. Accordingly, the present invention also provides a computer assisted program for performing the aforementioned steps in any of the embodiments concerning preparation of the subject probes. Further provided are computer readable medium (e.g., any medium used for storing data and/or software programs and instructions such as tapes, CDs, flash memory card and device, RAM and the like). A software program may optionally further incorporate the melting temperature contributions of selected CEPH labels to the melting temperature of the oligonucleotide sequence of a probe of the present invention.

Selecting a nucleotide sequence complementary to a region of the target can be done using any of the known software programs, e.g., Primer Express from ABI (Foster City, Calif.). Because the melting temperature of a suitable oligonucleotide sequence for a probe of the invention can be much lower than what has been conventionally considered to be ideal, some commercial software programs such as Primer Express may not even permit one to select an oligonucleotide probe sequence having a melting temperature lower than 60° C. It is commonly known that in order for the 5'-exonuclease to digest a probe, the probe must be first annealed to its complementary nucleic acid before the primer extension reaction reaches the probe hybridization site. To ensure such a condition for probe digestion, U.S. Pat. No. 5,210,015 describes that the labeled probe should be designed to have a higher melting temperature than the primer via methods such as increasing the length or GC content of the probe. Templeton and Class teach that the best $T_m$ for primers should be from about 55 to about 60° C. while the $T_m$ for the corresponding probes should be 7-10° C. higher (Katherine E. Templeton and Eric C. J. Class in *PCR Primers-A Laboratory Manual;* $2^{nd}$ ed; Carl W. Dieffenbach and Gabriela S. Dveksler, Cold Spring Harbor Laboratory: New York, 2003; pp 187-197). Furthermore, the PCR Assay Design Guideline established by Applied Biosystems (Foster city, Calif.) states that the calculated $T_m$ for the oligonucleotide selected for preparing a probe should be 68-70° C. and the $T_m$ for the corresponding primers should be 58-60° C. (PE Biosystem PCR technical manual). The PE PCR technical manual generally suggests that probe $T_m$ be 8-10° C. higher than that of the primers to ensure full probe hybridization during primer extension. In fact, the widely used commercial software for probe and primer design, Primer Express, from Applied Biosystems uses a default melting temperature of 70° C. for probe design and actually prevents one from changing the default temperature to below 60° C. All of these existing methods are distinct from the methods of preparing the probes of the present invention.

When the existing program does not permit one to select an oligonucleotide probe sequence having a melting temperature lower than 60° C., one may start with a computer-selected sequence and then manually truncate the sequence by taking away a certain number of nucleotides from either terminus or both termini until a sequence of desired melting temperature is obtained. In general, when truncating an oligonucleotide of a conventional calculated melting temperature, one may wish to keep the GC content of the truncated sequence as high as possible by preferentially truncating any AT-rich terminus or termini of the conventional probe sequence. As a result, in some instances, a probe of the invention may frequently contain a G or C at one of the termini or both termini. For a probe of the invention comprising two terminally attached reporter dyes, hybridization of the probe to a target sequence may, though not required, bring the dyes very close to a G for PET-related fluorescence quenching, accounting for the negative hybridization signal observed for some of the probes according to the invention.

Each of the two labels of the probe may be attached to any of the possible sites on the oligonucleotide, including any of the bases, any of the phosphate sites on the backbone, the 5-hydroxy group at the 5'-terminus and the 3'-hydroxy group at the 3'-terminus, provided that the two labels are separated by at least, 5, 6, 7, 8, 9, 10, 11, 12, 13, 14, 15, 20, 25, or more nucleotides. Preferably, the at least one reporter dye is attached to the 5'-terminus of the probe. More preferably, the at least one reporter dye is attached to the 5'-terminus and the other label is attached to the 3'-terminus of the probe. When any of the two labels is attached to an internal nucleotide, the label is preferably attached to the base of the nucleotide, preferably a thymidine base, via a flexible linker. When a suitable label is attached to the 5'-terminus, it is preferably attached to the 5'-hydroxy group via a variety of commercially available linkers. Similarly, when a suitable label is attached to the 3'-terminus, it is preferably attached to the 3'-hydroxy group via a variety of commercially available linkers.

A suitable linker mentioned herein to connect a suitable label and the oligonucleotide may comprise a linear or branched, saturated or unsaturated C2-C18 hydrocarbon linker, optionally comprising at least one of the heteroatoms selected from the group consisting of halogen, N, O, S and P. Typically, the linkers at the 5'- or 3'-terminus comprise a phosphate linkage formed between the oxygen atom of the 5'- or 3'-hydroxy group and the linker. Depending on the route of synthesis, the linker molecules may be derived from either the oligonucleotide or the labels. In other words, the each linker molecule may be part of the label molecule or part of the oligonucleotide which has incorporated the linker during the oligonucleotide synthesis.

The covalent attachment of labels to nucleic acids can be achieved by a variety of methods known to those of skill in the art. The covalent attachment of labels to nucleic acids is reviewed in Davies et al. (2000) Chem. Soc. Rev. 29:97-107, which is incorporated herein by reference in its entirety. Examples include, but are not limited to: incorporation of the labels during the synthesis of nucleic acids, typically solid phase synthesis, and post-synthetic labeling of either synthetic nucleic acids.

The incorporation of labels into oligonucleotides using solid phase synthetic methods entails the conversion of the labels into their phosphoramidite derivatives, which are then employed in the phosphoramidite solid phase synthetic method similar to nucleoside phosphoramidites. Using this method, the amidite derived from a particular dye is mixed with an activator such as 1H-tetrazole or 4,5-dicyanoimidazole, in a suitable solvent, and reacted with a hydroxy group of a support bound oligonucleotide to form a covalent phosphodiester bond between the oligonucleotide and the label. The attachment of labels using the phosphoramidite method is reviewed by Beaucage et al. (1993) Tetrahedron 49:1925-63 (1993), which is incorporated herein by reference in its entirety.

Post-synthetic labeling of synthetic nucleic acids or nucleic acids derived from enzymatic reactions involves the incorporation of functional groups into the nucleic acids, which serve as anchor points for the attachment of labels. The label is then derivatized with a chemical group or moiety that can be reacted with the functional group of the nucleic acid to promote the formation of a covalent bond between the nucleic acid and the label. The functional group incorporated into the nucleic acid can be any group that is capable of reacting selectively with the group or moiety that is incorporated into the label. Methods known to those skilled in the art to promote a covalent bond between a nucleic acid and a label are reviewed by Grimm et al. (2000) Nucleosides & Nucleotides 19:1943-65, which is incorporated herein by reference in its entirety A partial listing of reactive functionalities which can be used to modify labels for attachment to an oligonucleotide or spacer attached therein is found in Table 2.

TABLE 2

Reactive functionalities of use in labels and linkers

| Electrophilic Group | Nucleophilic Group | Resulting Covalent Linkage |
| --- | --- | --- |
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | esters |
| alkyl sulfonates | thiols | thioethers |
| alkyl sulfonates | carboxylic acids | esters |
| alkyl sulfonates | alcohols/phenols | esters |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carboxylic acids | amines/anilines | carboxamides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioethers |
| haloacetamides | thiols | thioethers |
| halotriazines | amines/anilines | aminotrizaines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

For example, a label may be modified to contain an active ester which will react with an amine to form a carboxamide linking the label to the oligonucleotide. Activated esters, may have the formula —COΩ, where Ω is a good leaving group (e.g. succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$ where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl. Other reactive functional groups which can be used to modify label molecules in preparation for attachment to an oligonucleotide probe of the invention, also include but are not limited to: acrylamide, an acyl nitrile, an alkyl halide, an amine, an anhydride, an aniline, an arylhalide, an azide, an aziridine, a carboxylic acid, a haloacetamide, a halotriazine, a hydrazine; a hydrazide, an imido ester, an isocyanate, an isothiocyanate, a maleimide, a phosphoramidite, a sulfonyl halide or a thiol. Other reactive groups include succinimidyl ester, an amine, a haloacetamide, a hydrazine, an isothiocyanate, maleimide, or a phosphoramidite. Alternatively, the label may contain an acyl azide which will react with an amine to form a carboxamide linking the label to the oligonucleotide. In other embodiments, the label may be functionalized to contain an aldehyde or ketone which can react with a hydrazine on a linker on an oligonucleotide to form a hydrazone linking the label to the oligonucleotide probe. In other embodiments, a label may contain an isocyanate which can react with an amine or alcohol on a linker on an oligonucleotide to form an urethane linking the label to the oligonucleotide probe. The labels may be modified to introduce either an electrophilic or nucleophilic group, a partial list of which are shown in Table 2. The modifications described herein do not limit the type of functionalities capable of being used to attach a dye to a linker attached to an oligonucleotide or directly to an oligonucleotide of the invention.

There are many other forms of modifier reagents on a solid support that can be used to introduce an amine with a variety of spacers, or to introduce a different reactive group, i.e., thiol or diene functionalities with similar spacer moieties, in order to link fluorescent dyes to the probes of the invention. Appropriate linking methodologies for dye attachment to oligonucleotides are described in many references, e.g., Khanna et al. (cited above); Marshall, Histochemical J., 7: 299-303 (1975); Menchen et al., U.S. Pat. No. 5,188,934; Menchen et al., European Patent Application 87310256.0; and Bergot et al., International Application PCT/US90/05565, Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink.™ II available from Applied Biosystems, Foster City, Calif.) Stabinsky, U.S. Pat. No. 4,739,044 (3' aminoalkylphosphoryl group); Agrawal et al., Tetrahedron Letters. 31: 1543-1546 (1990) (attachment via phosphoramidate linkages); Woo et al., U.S. Pat. No. 5,231,191; and Hobbs, Jr., U.S. Pat. No. 4,997,928. Sproat et al., Nucleic Acids Research, 15: 4837 (1987) (5' mercapto group); Nelson et al., Nucleic Acids Research, 17: 7187-7194 (1989) (3' amino group); and the like, all of which are incorporated by reference in their entirety. A number of linking moieties that can be attached to an oligonucleotide during synthesis, are commercially available, e.g., from Clonetech Laboratories (Palo Alto, Calif.), Biosearch (Novato, Calif.), Glen Research, and Applied Biosystems (Foster City, Calif.).

In some embodiments of the invention, amine-functionalized oligonucleotides were synthesized by using a CPG-supported amino modifier and appropriate phosphoramidite reagents containing a protected amine during the normal automated oligo synthesis.

A number of commercially available CPG-supported amino-modifiers with different spacer arms can be used to introduce an amino group at the 3' end of the dual labeled oliogonucleotides of the invention. The CPG-supported amino modifier, 3'-amino-modifier C7 CPG, was used in some of the examples listed in Table 1 and it has a structure as in Formula 3: Modifiers of this class are available which introduce spacers ranging from C3 to C7 groups.

Formula 3: The modification provides L$_1$ spacer

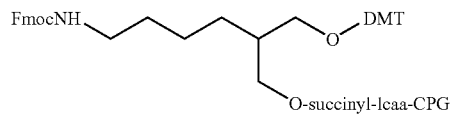

Fmoc and DMT were used as protecting groups for the amine and hydroxy groups, respectively, and "succinyl-lcaa" is a spacer between the solid support and the modifier. The base-labile Fmoc group was removed during ammonium treatment which also removes the oligonucleotide from CPG support. Introduction of the 3'-amino-modifier of Formula 3 incorporated a 7-carbon branched spacer between the amine group and the 3'-end phosphate, referred herein as L$_1$.

In some of the embodiments of the invention, phosphoramidites of protected amino-deoxynucleosides, i.e. for example, phosphoramidite of trifluoroacetylamino-2'-deoxythymidine, or amino-modifier C6 dT, were used for making T-modified oligonucleotides in some examples given in Table 1. The structure of amino-modifier C6 dT is shown in Formula 4: This reagent introduces a 10-atom linear aliphatic spacer between dT and the amine group, or between dT and a dye. The 10 carbon spacer introduced is referred herein as L$_2$. Other linkers of general type as modified C6 dT can be used to introduce spacers with different lengths or configurations. Linkers of this class can contain linker modification including cyclic, heterocyclic, aromatic, or heteroaromatic groups as part of the spacer in order to introduce rigidifying elements as part of the spacer, which also introduces a reactive group such as an amine, a thiol, a carboxylic acid, an active ester and the like, to label the oligonucleotide probe.

Formula 4: The modification extending from the pyrimidine ring is L$_2$ spacer

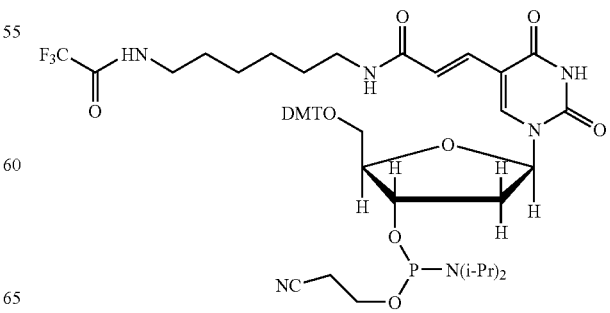

An amine functionality with various spacers can be introduced to the 5'-end by using a phosphoramidite of a protected amine at the last step of the automated synthesis. Two amino modifier reagents, 5'-amino-modifier C6-TFA (Formula 5) and 5'-amino-modifier C12 (Formula 6), were used for synthesizing 5'-end labeled oligonucleotides in Table 1. The structures are shown below:

Formula 5: The modification provides $L_3$ spacer

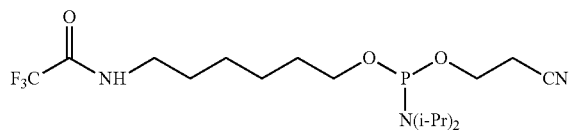

Formula 6: The modification provides $L_4$ spacer

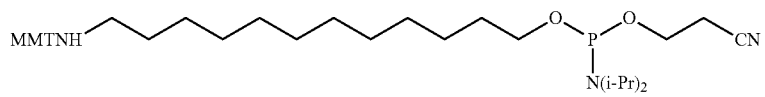

The linear 6-carbon spacer of 5'-amino-modifier C6-TFA is referred to herein as $L_3$, and similarly the linear 12-carbon spacer of 5'-amino-modifier C12 is referred to herein as $L_4$. In other embodiments of the invention, a linker modification may include cyclic, heterocyclic, aromatic, or heteroaromatic groups as part of the spacer in order to introduce rigidifying elements as part of the spacer, which also introduces a reactive group such as an amine, a thiol, a carboxylic acid, an active ester and the like, to label the oligonucleotide probe. The linkers used in the probes of the invention may further have other modifications present, such as the nucleophilic groups or electrophilic groups listed in Table 2 to facilitate the attachment of a label to an oligonucleotide.

Another method of enzymatically incorporating labels into nucleic acids is the use of label-conjugated nucleoside triphosphates in primer elongation reactions. This method is used extensively in modifications of the Sanger sequencing method for nucleic acids, as reviewed by Kashdan et al. in "Recombinant DNA Principles Methodologies," Greene and Rao (eds), Dekker 1998, NY, which is incorporated herein by reference. Other methods take advantage of the enzymes T4 polynucleotide kinase or deoxynucleotidyl transferase, which incorporate label-conjugated nucleosides through their triphosphates at the 5'-end or the 3'-end of the nucleic acid, respectively.

Once the oligo sequence, labels and label attachment positions have been decided, the actual synthesis of a probe of the invention can be readily carried out by one of skills using any of the known methods for preparing labeled oligonucleotides. Such methods include without limitation those described in U.S. Pat. No. 6,258,569 and the following references: Connolly et al., *Nucleic Acids Res.* (1985); Dreyer et al., *Proc. Natl. Acad. Sci.* (1985); Nelson et al., *Nucleic Acids Res.* (1989); Sproat et al., *Nucleic Acids Res.* (1987) and Zuckerman et al., *Nucleic Acids Res.* (1987). For probes having two different labels, it may require separate labeling steps. For example, the first label is typically attached to an oligonucleotide, either by starting the oligonucleotide synthesis with a protected label linked to a CPG solid support via a linker, or by incorporating the label during the oligonucleotide synthesis by using a labeled nucleoside (or deoxynucleoside) phosphoramidite. The second label molecule is attached to the oligonucleotide by using a labeled nucleoside phosphoramidite during the standard oligo synthesis. Alternatively and more typically, the second label molecule is attached to the oligo by first incorporating an amino group into the oligo during the oligo synthesis and then reacting a succinimidyl ester label with the amine-modified oligo. In yet another alternative method, the second label comprising a suitable linker molecule comprising a phosphoramidite group may be attached to the 5'-hydroxy group of the 5'-terminal nucleotide via standard phosphoramidite chemistry on a solid support. The above methods can also be applied to the synthesis of a probe comprising two identical labels according to the invention. More commonly, in contrast to the multi-step labeling procedures described above, a probe comprising two identical labels according to one embodiment of the present invention requires only a single labeling step to conjugate both labels to the oligonucleotide.

Typically, two suitable linker molecules, each comprising an amine functional group, are incorporated into the oligonucleotide at two separate sites, respectively, using standard, automated phosphoramidite chemistry on a so-called "controlled pore glass" (CPG) solid support. Various CPGs bearing a linker molecule comprising a protected amine group is widely commercially available. Similarly, various linker molecules comprising a protected amine group and a phosphoramidite group are also commercially available. Thus, incorporations of these linker molecules into the oligonucleotide can be readily carried out during the synthesis of the oligonucleotide on an oligonucleotide synthesizer using the well-practiced phosphoramidite chemistry. Once the suitable oligonucleotide containing the two suitable functional groups is prepared, it is then reacted with a suitable label having a suitable reactive group capable of reacting with the functional groups of the oligonucleotide to make a covalent bond. A preferred functional comprises primary aliphatic amines and thiols. Where desired, the functional groups comprising primary aliphatic amines can be employed. The preferred reactive group on selected labels according to the invention is succinimidyl ester (SE). Many suitable labels having a SE reactive group are commercially available from Biotium (Hayward, Calif.) or can be manufactured by one skilled in the art. Labeling of an amine-functionalized oligonucleotide according to the invention with a suitable label having a SE group is typically carried out by mixing an excess of the reactive label with the functionalized oligonucleotide in a suitable buffer such as a pH 8.5~9 0.1 M sodium bicarbonate buffer or the like at a temperature from about 4° C. to about room temperature for 1~2 hour time. The labeled oligonucleotide is isolated by gel filtration and further purified by HPLC, merely by way of example. Further details on the syntheses of homo-dually labeled probes can be found in US patent application No. 20050272053 and the specific examples illustrated in the Example Section of this disclosure.

The oligonucleotide portion of the probes of the invention can comprise DNA, RNA, single-stranded or double-stranded and any chemical modifications thereof, such as PNA and LNA. Modifications include, but are not limited to, those that provide other chemical groups that incorporate additional charge, polarizability, hydrogen bonding, electrostatic interaction, and functionality to the individual nucleic acid bases or to the nucleic acid as a whole. Such modifications include, but are not limited to, modified bases such as 2'-position sugar modifications, 5-position pyrimidine modifications, 8-position purine modifications, modifications at cytosine exocyclic amines, substitution of 5-bromo-uracil; backbone modifications, methylations, unusual base-pairing combinations such as the isobases isocytidine and isoguanidine and the like. Modifications can also include 3' and 5' modifications such as capping. The oligonucleotide probes of the present invention may include, in addition to the "natural" phosphodiester linkages, phosphorothioates and methylphosphonates. The nucleic acid can be derived from a completely chemical synthesis process, such as a solid phase mediated chemical synthesis, or from a biological origin, such as through isolation from almost any species that can provide DNA or RNA, or from processes that involve the manipulation of nucleic acids by molecular biology tools, such as DNA replication, PCR amplification, reverse transcription, or from a combination of those processes.

The subject oligonucleotide probe may comprise less than about 50 nucleotide bases, preferably less than 25 nucleotides, or between about 5 to about 25 nucleotides, between about 10 to about 25 nucleotides, between about 10 to about 15 nucleotides, or between about 17 to about 25 nucleotides.

Probes prepared by the methods of the present invention exhibit high performance sensitivity in a quantitative amplification reaction. For example, FIGS. 1-5 show PCR signal comparisons between various probes according to the present invention and various conventional probes in amplifying a spectrum of different gene fragments. In particular, some of the probes of the invention (i.e., SEQ ID NOs 8, 13, 14 and 25) have a calculated melting temperature below or significantly below 60° C. or have a length below 20 nucleotides, but they still exhibited good high signal to noise ratio.

As shown in Table 1, the actual melting temperatures for probes of SEQ ID NOs 7, 8, 12, 13 and 45, as measured by monitoring the fluorescence change of the reporter dyes during probe melting, are all around or above 70° C. (Table 1). Therefore, despite the low calculated melting temperature, the actual melting temperatures of the probes according to the invention are higher, ensuring proper hybridization of the probes. The result suggests that the pair of rhodamine dyes attached to these probes contributed to the observed melting temperature increase.

Probes prepared by the methods of the present invention exhibit less inhibition of template-dependent polymerization reactions such as end-point and real-time PCR. MGB probes are known to show PCR inhibition under certain conditions. As an example, FIG. 7 shows the comparison of a probe of the invention (CR*GAPDH*CR, SEQ ID NO: 8) and a CDPI-containing MGB probe (ABI Cat #4352934E) at three different probe concentration (1×, 2× and 3×) in the amplification of a GAPDH gene fragment. The signal intensity associated with the probe of the invention increased proportionally as the probe concentration increased from 1× to 3×. On the other hand, increasing the concentration of the MGB probe from 1× to 2× caused a significant delay in Ct value. This drawback was even more pronounced when the MGB probe concentration was raised to 3×, no PCR signal was detectable.

Without being bound by any particular theory, the probes prepared by the present invention and especially those having two identical dyes may produce very weak or undetectable signal, or even more commonly, negative signal at the moment when hybridization with a target nucleic acid occurs (i.e., prior to the cleavage by an enzyme with 5' to 3' exonuclease activity, if present in the reaction). Conventional probes described in U.S. Pat. Nos. 5,538,848 and 6,258,569; and US patent application No. 20050272053 typically produce a substantially positive signal at the time of hybridization, as expected due to the very large physical separation between the reporter dye and the quencher following the hybridization (SEQ ID NOS: 46 and 47 in FIG. 12). While the probes of the invention are expected to assume a random conformation before hybridizing to a target, the two labels on the probe are in close proximity to cause fluorescence quenching. On hybridization to a target nucleic acid, the probe becomes relatively extended and as a result the two labels on the probe are separated by a greater distance. However, unlike TaqMan® probes, certain exemplary probes of the present invention may produce a very weak positive signal (SEQ ID NOS: 28 and 35 in Figure SEQ ID NO: 40 in FIG. 11; and SEQ ID NO: 45 in FIG. 12), no detectable signal (SEQ ID NOS: 11 and 14 in FIG. 9; SEQ ID NOS: 39 and 41 in FIG. 11; and SEQ ID NO: 44 in FIG. 12), or a negative signal (SEQ ID NOS: 5, 6, 7, 8 and 9 in FIG. 8; SEQ ID NOS: 10, 12 and 13 in FIG. 9; and SEQ ID NO: 32 in FIG. 10). Without being bound by any particular theory, there may exist an interplay of two separate fluorescence quenching mechanisms associated with the unique design of the probe of the invention. The first fluorescence quenching mechanism may relate to the FRET-based fluorescence quenching, which is reduced as the two labels become physically more separated upon probe hybridization. However, since the probe of the present invention is generally much shorter than a TaqMan® probe, for example, the two labels on the probe are not separated as far away as the two labels on a TaqMan® probe. As a result, the fluorescence release of the probe from this process is generally smaller than that observed with the conventional TaqMan® probes. The second mechanism of fluorescence quenching is believed to be related to the interaction between the reporter dyes and guanosine (G) nucleotides in the target DNA following probe hybridization. It is known that guanosine (G) is capable of acting as a quencher that can quench the fluorescence of a nearby fluorescent dye through photo-induced electron transfer (PET) (Knemeyer et al. *Anal. Chem.* 72:3717-3724 (2000)). Since the reporter CEPH dyes according to the present invention are capable of interacting with DNA, such interaction may bring the dyes close to an electron-rich base such as a G base for efficient PET-related fluorescence quenching. Thus, although hybridization of the probe of the invention may partially release the fluorescence of the dyes as a result of the reduced FRET-based quenching, fluorescence quenching by a G base through PET effect may substantially cancel out the released fluorescence, resulting in weak, undetectable or, more frequently, negative signals. Regardless of the nature and magnitude of the hybridization signal, however, a probe of the present invention is highly sensitive and specific when used in monitoring nucleic acid amplification involving 5'-exonuclease activity as demonstrated in FIGS. 1-7.

Uses of the Subject Probes:

The subject probes provide an effective means for detection and/or quantification of target nucleic acids. The detection and/or quantification methods have a broad spectrum of utility in, e.g. drug screening, disease diagnosis and treatment monitoring, phylogenetic classification, genotyping individuals, parental and forensic identification. At a fundamental level, the detection and/or quantification methods can facilitate identification and quantification of differential gene expression between diseased and normal tissues, among different types of tissues and cells, amongst cells at different developmental stages or at different cell-cycle points, and amongst cells that are subjected to various environmental stimuli or lead drugs. In addition, the subject detection and/or quantification methods can facilitate identification and quantification of genetic mutations, including but not limited to chromosomal abnormalities (deletions, insertions and/or translocations) and single nucleotide polymorphisms (SNP). Furthermore, the subject methods can facilitate veterinary diagnostics and agricultural genetics testing involving samples from a non-human animal or a plant species, which provides a means of quality control for agricultural genetic products and processes; environmental testing, organisms and their toxins analysis utilizing samples of soil, water, air, etc.; food testing includes the quantitation of organisms, e.g. bacteria, fungi, etc., as a means of quality control; industrial process monitoring where nucleic acids are detected and/or quantified to indicate proper control of a production process; and insurance testing where organisms and/or their toxins are identified in screening tests to determine the risk category of an insured.

In one embodiment of the invention, a method is provided for detecting or quantifying a target nucleic acid, the method comprising the steps of: a) providing a probe of the present invention; b) contacting said probe with the nucleic acid target so as to allow for hybridization of the probe with the nucleic acid target; and c) detecting or quantifying said nucleic acid target by measuring a change in the fluorescence of the probe upon the hybridization of the nucleic acid probe with the nucleic acid target.

As used herein, hybridization occurs when the probe form a complex with the target nucleic acid. In general, the complex is stabilized, at least in part, via hydrogen, bonding between the bases of the nucleotide residues. The hydrogen bonding may occur by Watson-Crick base pairing, Hoogstein binding, or in any other sequence-specific manner. Hybridization may constitute a step in a more extensive process, such as the initiation of a PCR reaction, or the enzymatic cleavage of a polynucleotide by a ribozyme.

After hybridization between the probe and the target has occurred, a change in the intensity of the fluorescence of the probe is measured. Such change before and after hybridization can yield a positive gain or negative reduction in the detected signal intensity. Depending on the specific hybridization assay that is run, more than one event after hybridization may contribute to the generation of a change in signal intensity. For example, an increase in reporter signal may result by way of spatial extension or separation of the reporter dye from the quencher dye while both are still attached to the probe. In addition, either the reporter or the quencher dye of the probe can be separated by way of cleavage via an enzyme (e.g., a polymerase having a 5' to 3' exonuclease), thereby generating a reporter signal that is detected. As noted above, both the reporter and the quencher dyes are defined in functional terms, such that these dyes can be identical though serving, relative to each other, a different function when used in a hybridization reaction. For example, a dye attached to a probe is a quencher because it reduces the emission of an optical signal when the probe is not hybridized with the target nucleic acid (typically when the probe assumes a random state). The same dye can become a reporter dye once upon being cleaved by an enzyme after hybridization with the target nucleic acid as the signal of the dye is now detected during the assay.

A change of signal intensity can be detected by any methods known in the art and is generally dependent on the choice of dyes used. It can be performed with the aid of an optical system. Such system typically comprises at least two elements, namely an excitation source and a photon detector. Numerous examples of these elements are available in the art. An exemplary excitation source is a laser, preferably a polarized laser. The choice laser light will depend on the fluorophores attached to the probe. For most of the fluorescent compounds, the required excitation light is within the range of about 300 nm to about 700 nm. Those skilled in the art can readily ascertain the appropriate excitation wavelength to excite a given fluorophore by routine experimentation (see e.g., The Handbook—'A Guide to Fluorescent Probes and Labeling Technologies, Tenth Edition' (2005) (available from Invitrogen, Inc./Molecular Probes) previously incorporated herein by reference). Where desired, one can employ other optical systems especially for multiplex hybridization assays. These optical systems may comprise elements such as optical reader, high-efficiency photon detection system, photo multiplier tube, gate sensitive FET's, nano-tube FET's, photodiode (e.g. avalanche photo diodes (APD)), camera, charge couple device (CCD), electron-multiplying charge-coupled device (EMCCD), intensified charge coupled device (ICCD), and confocal microscope. These optical systems may also comprise optical transmission elements such as optic fibers, optical switches, mirrors, lenses (including microlens and nanolens), collimators. Other examples include optical attenuators, polarization filters (e.g., dichroic filter), wavelength filters (low-pass, band-pass, or high-pass), waveplates, and delay lines. In some embodiments, the optical transmission element can be planar waveguides in optical communication with the arrayed optical confinements. These and other optical components known in the art can be combined and assembled in a variety of ways to effect detection of the distinguishable signals emitted from the hybridization reaction.

The method described above can be applied to nucleic acid amplification in which the target nucleic acid is increased in copy number. Such increase may occur in a linear or in an exponential manner. Amplification may be carried out by natural or recombinant DNA polymerases such as Taq polymerase, Pfu polymerase, T7 DNA polymerase, Klenow fragment of E. coli DNA polymerase, Tma DNA polymerase, exo-Tli DNA polymerase, exo-KOD DNA polymerase, exo-JDF-3 DNA polymerase, exo-PGB-D DNA polymerase, UlTma (N-truncated) Thermatoga martima DNA polymerase, Sequenase, and/or RNA polyinerases such as reverse transcriptase.

A preferred amplification method is polymerase chain reaction (PCR). General procedures for PCR are taught in U.S. Pat. Nos. 4,683,195 (Mullis) and U.S. Pat. No. 4,683,202 (Mullis et al.). Briefly, amplification of nucleic acids by PCR involves repeated cycles of heat-denaturing the DNA, annealing two primers to sequences that flank the target nucleic acid segment to be amplified, and extending the annealed primers with a polymerase. The primers hybridize to opposite strands of the target nucleic acid and are oriented so that the synthesis by the polymerase proceeds across the segment between the primers, effectively doubling the amount of the target segment. Moreover, because the extension products are also complementary to and capable of binding primers, each successive cycle essentially doubles the amount of target nucleic acids synthesized in the previous cycle. This results in exponential accumulation of the specific target nucleic acids at approximately a rate of 2°, where n is the number of cycles.

A typical conventional PCR thermal cycling protocol comprises 30 cycles of (a) denaturation at a range of 90° C. to 95° C. for 0.5 to 1 minute, (b) annealing at a temperature ranging from 50° C. to 65° C. for 1 to 2 minutes, and (c) extension at 68° C. to 75° C. for at least 1 minute. Other protocols including but not limited to universal protocol as well as fast cycling protocol can be performed the subject probes as well.

A variant of the conventional PCR is a reaction termed "Hot Start PCR". Hot Start PCR techniques focus on the inhibition of polymerase activity during reaction preparation. By limiting polymerase activity prior to PCR cycling, non-specific amplification is reduced and the target yield is increased. Common methods for Hot Start PCR include chemical modifications to the polymerase (see, e.g., U.S. Pat. No. 5,773,258), inhibition of the polymerase by a polymerase-specific antibody (see, e.g., U.S. Pat. No. 5,338,671), and introduction of physical barriers in the reaction site to sequester the polymerase before the thermal cycling takes place (e.g., wax-barrier methods). The reagents necessary for performing Hot Start PCR are conveniently packaged in kits that are commercially available (see, e.g., Sigma's JumpStart Kit).

Another variation of the conventional PCR that can be performed with the subject probes is "nested PCR" using nested primers. The method is preferred when the amount of target nucleic acid in a sample is extremely limited for example, where archival, forensic samples are used. In performing nested PCR, the nucleic acid is first amplified with an outer set of primers capable of hybridizing to the sequences flanking a larger segment of the target nucleic acid. This amplification reaction is followed by a second round of amplification cycles using an inner set of primers that hybridizes to target sequences within the large segment.

The subject probes can be employed in reverse transcription PCR reaction (RT-PCR), in which a reverse transcriptase first coverts RNA molecules to double stranded cDNA molecules, which are then employed as the template for subsequent amplification in the polymerase chain reaction. In carrying out RT-PCR, the reverse transcriptase is generally added to the reaction sample after the target nucleic acids are heat denatured. The reaction is then maintained at a suitable temperature (e.g., 30° C.-45° C.) for a sufficient amount of time (e.g., 5-60 minutes) to generate the cDNA template before the scheduled cycles of amplification take place. Such reaction is particularly useful for detecting the biological entity whose genetic information is stored in RNA molecules. Non-limiting examples of this category of biological entities include RNA viruses such as HIV and hepatitis-causing viruses. Another important application of RT-PCR embodied by the present invention is the simultaneous quantification of biological entities based on the mRNA level detected in the test sample.

The subject probes can also be employed to perform ligase chain polymerase chain reaction (LCR-PCR). The method involves ligating the target nucleic acids to a set of primer pairs, each having a target-specific portion and a short anchor sequence unrelated to the target sequences. A second set of primers containing the anchor sequence is then used to amplify the target sequences linked with the first set of primers. Procedures for conducting LCR-PCR are well known to artisans in the field, and hence are not detailed herein (see, e.g., U.S. Pat. No. 5,494,810).

The subject probes are particularly suited for use in a homogeneous assay. In such an assay, a target nucleic acid is detected and/or quantified without the requirement of post-assay processing to record the result of the assay. For example, a homogeneous PCR reaction can be carried out in a closed sample holder (e.g., a tube, a sample capillary or thermalchip), and no further addition or removal of reagents is necessary to record the result once the assay is started. Homogeneous assays allow recordation of the result of the assay in real time. Where desired, in practicing the subject methods, the result of the assay can be continuously recorded as the assay progresses in time or recorded intermittently at one or more point during the assay or upon completion of the assay.

Where desired, homogeneous assays can be multiplexed, i.e., more than one target nucleic acid can be detected in one assay. In a multiplex assay, two or more specific nucleic acid probes, which differ in the nature of their covalently attached dyes, are added to the mixture to be assayed. The dyes are chosen to produce distinguishable fluorescent signals from each specific nucleic acid probe. The signals of the different dye combinations of the nucleic acid probes can be recorded simultaneously to detect and/or quantify the corresponding target nucleic acids. Multiplexing greatly reduces the cost of analysis and can tremendously increase throughput in high volume settings.

The subject probes can be used to detect single mutations. Accordingly, methods are provided to use the probes of the invention to detect as few as a single mismatch between the probe sequence and a target sequence. Such high specificity in nucleic acid detection by PCR is highly valuable in clinical diagnosis and genetic research. For example, many diseases are associated with single mutations at different sites in the human genome. Although in theory this type of genetic variations, also called single nucleotide polymorphism or SNP, may be detected by sequencing, such sequencing method is not expected to be practical on a large scale due to high cost and low efficiency. Detection of SNP by an amplification reaction is feasible with the use of the subject probes. As shown in FIG. 6, a probe comprising either a reporter-reporter pair (FIG. 6, Panel A) (SEQ ID NO 8) or a reporter-quencher pair (FIG. 6. Panel B) (SEQ ID NO 9) according to the invention successfully detects a single base variation in the target. In particular, the probe comprising two identical rhodamine 110 reporter dyes (CR110 or CR) (FIG. 6. Panel A) showed exceptionally high specificity by producing no detectable signals at all for the mismatched targets.

The subject probes are also particularly suited for monitoring nucleic acid amplification reactions. In a related embodiment, the present invention provides a method of monitoring the increase in a target nucleic acid during amplification of said target. The method typically involves a) providing an amplification reaction mixture that comprises said target nucleic acid, at least one primer that hybridizes to the target nucleic acid, a labeled oligonucleotide probe of the present invention that provides a detectable signal, the intensity of which is proportional to the increase in the target nucleic acid in the amplification; (b) treating said mixture under conditions for amplifying said target nucleic acid; and (c) measuring the amount of said signal produced by said mixture during said treating step (c). Where desired, the amount of signal is determined continuously throughout the amplification reaction or determined intermittently during the amplification reaction. The amplification can be exponentially with the use of a primer pair or linearly with the use, of one primer of the pair.

The increase in signal intensity during the amplification reaction may due to the step of hybridization of the probe to the target nucleic acid and also the step of cleavage via the action of the polymerase utilized in the amplification reaction.

In one aspect, the subject methods exploit the 5' to 3' nuclease activity of a polymerase when used in conjunction with PCR. When the subject probe is added concomitantly with the primer at the start of PCR, and the signal generated from hydrolysis of the labeled nucleotide(s) of the probe provides a means for detection of the target sequence during its amplification. Numerous polymerases are suited to catalyze primer and template-dependent nucleic acid synthesis and possess the 5' to 3' nuclease activity. Non-limiting examples include DNA polymerases such as *E. coli* DNA polymerase I, *Thermus thermophilus* (Tth) DNA polymerase, *Bacillus stearothermophilus* DNA polymerase, *Thermococcus littoralis* DNA polymerase, and *Thermus aquaticus* (Taq) DNA polymerase. Where desired, temperature stable polymerases can be employed in a nucleic acid amplification reaction. See, e.g., U.S. Pat. No. 4,889,818 that discloses a representative thermostable enzyme isolated from *Thermus aquaticus*. Additional representative temperature stable polymerases include without limitation, e.g., polymerases extracted from the thermostable bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima, Thermococcus littoralis*, and *Methanothermus fervidus*.

In another embodiment, nucleic acid amplification can be performed with polymerases that exhibit strand-displacement activity (also known as rolling circle polymerization). Strand displacement can result in the synthesis of tandem copies of a circular DNA template, and is particularly useful in isothermal PCR reaction. Non-limiting examples of rolling circle polymerases suitable for the present invention include but are not limited to T5 DNA polymerase (Chatterjee et al., Gene 97:13-19 (1991)), and T4 DNA polymerase holoenzyme (Kaboord and Benkovic, Curr. Biol. 5:149-157 (1995)), phage M2 DNA polymerase (Matsumoto et al., Gene 84:247 (1989)), phage PRD1 DNA polymerise (Jung et al., Proc. Natl. Aced. Sci. USA 84:8287 (1987), and au and Ito, Biochim. Biophys. Acta. 1219:267-276 (1994)), Klenow fragment of DNA polymerase I (Jacobsen et al., Eur. J. Biochem. 45:623-627 (1974)).

A preferred class of rolling circle polymerases utilizes protein priming as a way of initiating replication. Exemplary polymerases of this class are modified and unmodified DNA polymerase, chosen or derived from the phages Φ29, PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. Specifically, the wildtype bacteriophage Φ29 genome consists of a linear double-stranded DNA (dsDNA) of 19,285 base pairs, having a terminal protein (TP) covalently linked to each 5' end. To initiate replication, a histone-like viral protein forms a nucleoprotein complex with the origins of replication that likely contributes to the unwinding of the double helix at both DNA ends (Serrano et al., The EMBO Journal 16(9): 2519-2527 (1997)). The DNA polymerase catalyses the addition of the first dAMP to the hydroxyl group provided by the TP. This protein-primed event occurs opposite to the second 3' nucleotide of the template, and the initiation product (TP-dAMP) slides back one position in the DNA to recover the terminal nucleotide. After initiation, the same DNA polymerase replicates one of the DNA strands while displacing the other. The high processivity and strand displacement ability of Φ29 DNA polymerase makes it possible to complete replication of the Φ29 TP-containing genome (TP-DNA) in the absence of any helicase or accessory processivity factors (reviewed by Serrano et al., The EMBO Journal 16(9): 2519-2527 (1997)).

Strand displacement can be enhanced through the use of a variety of accessory proteins. They include but are not limited to helicases (Siegel et al., J. Biol. Chem. 267:13629-13635 (1992)), herpes simplex viral protein ICP8 (Skaliter and Lehman, Proc. Natl. Acad. Sci. USA 91(22):10665-10669 (1994)), single-stranded DNA binding proteins (Rigler and Romano, J. Biol. Chem. 270:8910-8919 (1995)), adenovirus DNA-binding protein (Zijderveld and van der Vliet, J. Virology 68(2):1158-1164 (1994)), and BMRF1 polymerase accessory subunit (Tsurumi et al., J. Virology 67(12):7648-7653 (1993)).

The subject probes can be utilized in an isothermal amplification reaction. Such amplification reaction does not rely solely upon thermal cycling. The procedure can be applied at a wide range of ambient temperatures. In particular, denaturation of the double-stranded template sequence is not accomplished solely through an increase in temperature above the melting temperature of the double stranded sequence. Rather, the denaturation process involves physical or mechanical force that separates the strand to allow primer annealing and extension. Various mechanisms for conducting isothermal amplification reaction including isothermal PCR are described in US. Patent Publication No 20060019274 and U.S. Pat. Nos. 5,824,477 and 6,033,850, which are incorporated herein by reference.

Nucleic acid amplification is generally performed with the use of amplification reagents. Amplification reagents typically include enzymes, aqueous buffers, salts, primers, target nucleic acid, and nucleoside triphosphates. Depending upon the context, amplification reagents can be either a complete or incomplete amplification reaction mixture.

The choice of primers for use in nucleic acid amplification will depend on the target nucleic acid sequence. Primers used in the present invention are generally oligonucleotides, e.g., 10 to 100 or 10 to 25 bases in length, that can be extended in a template-specific manner via the action of a polymerase. In general, the following factors are considered in primer design: a) each individual primer of a pair preferably does not self-hybridize in an amplification reaction; b) the individual pairs preferably do not cross-hybridize in an amplification reaction; and c) the selected pair must have the appropriate length and sequence homology in order to anneal to two distinct regions flanking the nucleic acid segment to be amplified. However, not every nucleotide of the primer must anneal to the template for extension to occur. The primer sequence need not reflect the exact sequence of the target nucleic acid. For example, a non-complementary nucleotide fragment may be attached to the 5' end of the primer with the remainder of the primer sequence being complementary to the target. Alternatively, non-complementary bases can be interspersed into the primer, provided that the primer sequence has sufficient complementarily with the target for annealing to occur and allow synthesis of a complementary nucleic acid strand.

The primer pairs used in this invention can be obtained by chemical synthesis, recombinant cloning, or a combination thereof. Methods of chemical polynucleotide synthesis are well known in the art and need not be described in detail herein. One of skill in the art can use the target sequence to obtain a desired primer pairs by employing a DNA synthesizer or ordering from a commercial service.

A nucleic acid amplification reaction typically comprises a target nucleic acid in a buffer compatible with the enzymes used to amplify the target. The buffer typically contains nucleotides or nucleotide analogs (ATP, TTP, CTP, GTP, or analogs thereof including without limitation pentaphosphates having the respective base unit) that are capable of being incorporated into a replica strand of the template sequence.

Where desired, amplification reaction is carried out as an automated process. Numerous thermocyclers are available in the art that are capable of holding 48, 96 or more samples. A suitable optical system moves the excitation light from the source to the reaction sites and measures the emission light from each sample. For example, multiple fiber optic leads simultaneously read all PCR tubes undergoing thermocycling. However, only a single fluorometer may be needed to read fluorescence from the reaction sites. An analogous detection scheme is suitable in a 96-well microtiter format. This type of format is frequently desirable in clinical laboratories for large scale sample screening, for example, for genetic analysis such as screening for AIDS virus in blood bank screening procedures.

Accordingly, the present invention also provides an apparatus for detecting the signal generated by the subject probe, which can be used to detect, measure, and quantify the signal before, during, and after amplification. The apparatus comprises a thermal unit (e.g., a thermocycler) capable of holding an amplification reaction mixture comprising the subject probes and effecting an amplification of the target sequence, and a detector that detects the signal generated from the subject probes.

In another embodiment of the present invention, the subject probes are employed in assays that are conducted on nucleic acid microarrays to detect or quantify nucleic acid targets. In such assays, a fluorescent signal is generated on a nucleic acid microarray upon the presence of a complementary target nucleic acid.

Nucleic acid microarrays including gene chips comprise ordered arrays of nucleic acids that are covalently attached to a solid surface, see e.g., U.S. Pat. Nos. 5,871,928, 6,040,193, 6,262,776, 6,403,320, and 6,576,424. The fluorescent signal that is generated in the assay can be monitored and quantified with optical detectors including but not limited to fluorescence imagers, e.g. commercial instruments supplied by Hitachi Corp., San Bruno, Calif. or confocal laser microscopes (confocal fluorescence scanners), e.g. commercial instruments from General Scanning, Inc., Watertown, Mass.

In assays that are conducted on nucleic acid microarrays, the target nucleic acids may be provided as a mixture of nucleic acid sequences derived from any suitable biological sources. They can be derived from body fluid, solid tissue samples, tissue cultures or cells derived therefrom and the progeny thereof, and sections or smears prepared from any of these sources, or any other samples that contain nucleic acids.

Where expression pattern is assayed, the mRNA sequences are first typically amplified by reverse transcription PCR with universal primers prior to their use as the target sequences in the assay. In one embodiment, all nucleic acid sequences present in the test sample are simultaneously applied to the microarray for analysis, thus allowing the interaction of all target nucleic acid sequences with all nucleic acids that are present on the array. In another embodiment, the target nucleic acids applied to the array are pre-selected to yield a subset for refined hybridization analysis utilizing a microarray. For example, a limited number of target sequences can contain more than one stretch of specific nucleotide sequence to be analyzed, e.g. more than one single nucleotide polymorphism. The nucleic acid sequences of this setting may be amplified by PCR with the aid of specific primers prior to their analysis on the microarray.

In assaying for expression of multiples genes of a subject, target polynucleotides are allowed to form stable complexes with probes on the aforementioned arrays in a hybridization reaction. It will be appreciated by one of skill in the art that where antisense RNA is used as the target nucleic acid, the sequence immobilized on the array are chosen to be complementary to sequences of the antisense nucleic acids. Conversely, where the target nucleic acid pool is a pool of sense nucleic acids, the sequence immobilized on the array are selected to be complementary to sequences of the sense nucleic acids. Finally, where the nucleic acid pool is double stranded, the probes may be of either sense and/or antisense as the target nucleic acids include both sense and antisense strands.

In one embodiment, the subject probes are utilized to perform a competitive hybridization on a microarray. In this assay format, a target nucleic acid from a test sample competes with a probe of the present invention for binding of a known sequence immobilized on the microarray. The amount of labeled probes that will bind to the immobilized known sequences is inversely proportional to the concentration of corresponding target nucleic acids in the test sample.

A variant hybridization assay involves the use of polymerases on a microarray to enhance the signals of the probes by performing cleavage of the reporters. For example, a mixture of target sequences are first allowed to hybridize with known sequences immobilized on the array. Unhybridized sequences are then washed away. Thereafter, probes corresponding to the target sequences are allowed to hybridize to different regions on the targets. Upon washing of the excessive unbound probes, the reporter dyes on the hybridized probes are cleaved via the action of polymerases, thereby generating a detectable signal that is indicative of the presence and/or quantity of a target sequence initially present in the test sample.

Suitable hybridization conditions for the practice of the present invention are such that the recognition interaction between the sequence on the array and target is both sufficiently specific and sufficiently stable. As noted above, hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, for example, (Sambrook, et al., (1989), supra).

In general, there is a tradeoff between hybridization specificity (stringency) and signal intensity. In a preferred embodiment, washing the hybridized array prior to detecting the target-probe complexes is performed to enhance the signal to noise ratio. Typically, the hybridized array is washed at successively higher stringency solutions and signals are read between each wash. Analysis of the data sets thus produced will reveal a wash stringency above which the hybridization pattern is not appreciably altered and which provides adequate signal for the particular polynucleotide probes of interest. Parameters governing the wash stringency are generally the same as those of hybridization stringency. Other measures such as inclusion of blocking reagents (e.g. sperm DNA, detergent or other organic or inorganic substances) during hybridization can also reduce non-specific binding.

Imaging specific hybridization event on a microarray is typically performed with the aid of an optical system. Non-limiting examples of suitable systems include camera, charge couple device (CCD), electron-multiplying charge-coupled device (EMCCD), intensified charge coupled device (ICCD), and confocal microscope.

The microarray provides a positional localization of the sequence where hybridization has taken place. The position of the hybridized region correlates to the specific sequence, and hence the identity of the target expressed in the test sample. The detection methods also yield quantitative measurement of the level of hybridization intensity at each hybridized region, and thus a direct measurement of the level of expression of a given gene transcript. A collection of the data indicating the regions of hybridization present on an array and their respective intensities constitutes a hybridization pattern that is representative of a multiplicity of expressed gene transcripts of a subject. Any discrepancies detected in the hybridization patterns generated by hybridizing target polynucleotides derived from different subjects are indicative of differential expression of a multiplicity of gene transcripts of these subjects.

In one aspect, the hybridization patterns to be compared can be generated on the same array. In such case, different patterns are distinguished by the distinct types of detectable labels. In a separate aspect, the hybridization patterns employed for the comparison are generated on different arrays, where discrepancies are indicative of a differential expression of a particular gene in the subjects being compared.

The test nucleic acids for a comparative hybridization analysis can be derived from (a) cells from different organisms of the same species (e.g. cells derived from different humans); (b) cells derived from the same organism but from different tissue types including normal or disease tissues, embryonic or adult tissues; (c) cells at different points in the cell-cycle; (d) cells treated with or without external or internal stimuli. Thus, the comparative hybridization analysis using the arrays of the present invention can be employed to monitor gene expression in a wide variety of contexts. Such analysis may be extended to detecting differential expression of genes between diseased and normal tissues, among different types of tissues and cells, amongst cells at different cell-cycle points or at different developmental stages, and amongst cells that are subjected to various environmental stimuli or lead drugs. Therefore, the expression detecting methods of this invention may be used in a wide variety of circumstances including detection of disease, identification and quantification of differential gene expression between at least two samples, linking the differentially expressed genes to a specific chromosomal location, and/or screening for compositions that upregulate or downregulate the expression or alter the pattern of expression of particular genes.

The subject amplification and any other hybridization assays described herein can be used to detect any target nucleic acids from any sources suspected to contain the target. It is not intended to be limited as regards to the source of the sample or the manner in which it is made. Generally, the test sample can be biological and/or environmental samples. Biological samples may be derived from human or other animals, body fluid, solid tissue samples, tissue cultures or cells derived therefrom and the progeny thereof, sections or smears prepared from any of these sources, or any other samples that contain nucleic acids. Preferred biological samples are body fluids including but not limited to urine, blood, cerebrospinal fluid, spinal fluid, sinovial fluid, semen, ammoniac fluid, cerebrospinal fluid (CSF), and saliva. Other types of biological sample may include food products and ingredients such as dairy items, vegetables, meat and meat by-products, and waste. Environmental samples are derived from environmental material including but not limited to soil, water, sewage, cosmetic, agricultural and industrial samples, as well as samples obtained from food and dairy processing instruments, apparatus, equipment, disposable, and non-disposable items.

Preparation of Nucleic Acids Contained in the Test Sample can be Carried Out According to Standard Methods in the Art or procedures described. Briefly, DNA and RNA can be isolated using various lytic enzymes or chemical solutions according to the procedures set forth in Sambrook et al. ("Molecular Cloning: A Laboratory Manual", Second Edition, 1989), or extracted by nucleic acid binding resins following the accompanying instructions provided by manufacturers' instructions.

Reaction Mixtures and Kits of the Present Invention:

The present invention also provides a reaction mixture useful for amplification of a nucleic acid target comprises at least one oligonucleotide primer and a subject probe, wherein said primer primes the synthesis of a strand of said target, and wherein the probe hybridizes to a region of said target synthesizable by said primer. The reaction mixture may further comprise a pair of primer (forward and reverse) and/or a nucleic acid polymerase having a 5' to 3' nuclease activity.

The present invention further provides a kit for detecting a nucleic acid sequence comprising a reaction mixture of the invention and a nucleic acid polymerase. The kit may further comprise other reagents to effect hybridization of the probes with a given target nucleic acids. Reagents can be supplied in a solid form or dissolved/suspended in a liquid buffer suitable for inventory storage, and later for exchange or addition into the reaction mixture when the hybridization assay is performed. Suitable individual packaging is normally provided and instructions for users are generally supplied as well. Diagnostic or prognostic procedures using the kits of this invention can be performed by clinical laboratories, experimental laboratories, practitioners, or private individuals.

EXAMPLES

Example 1

Oligonucleotide Synthesis and Labeling

Materials and Equipment: All anhydrous solvents and phosphoramidite reagents including phosphoramidites of nucleosides and protected linkers were purchased from Proligo, Boulder, Colo. or Glen Research, Sterling, Va. All unlabeled and amine-modified oligonucleotides were synthesized on an Expedite 8909 oligonucleotide synthesizer by Applied Biosystems (Foster City, Calif.).

Primer and Probe design: Primer sequences were selected using the commercial software Primer Express from Applied Biosystems (Foster City, Calif.) or the public web-based software Primer3 (http://frodo.wi.mit.edu/cgi-bin/primer3/primer3_www.cgi). Detailed sequence information along with the computer-predicted melting temperatures for the primer sequences are listed in Table 1. Probe sequences having conventional melting temperatures were also selected using the same softwares. The conventional probe sequences were then systematically truncated by 2 to 10 nucleotides from 5'- or 3'-terminus, or a combination of 5'- and 3'-termini to produce a series of related shorter sequences, which were used for constructing a series of shorter dually labeled probes.

Each probe name in Table 1 consists of the name of the gene in the middle, a numerical number following the gene name indicating the number of nucleotides removed from the parent/conventional probe sequence, two "s" symbols indicating the linkage between each label and the oligonucleotide, and abbreviated name of the dye at the beginning and end of the probe name. CR, RG, FAM and TAM are the abbreviations for rhodamine 110, rhodamine 6G, fluorescein and tetramethylrhodamine (TAMRA), respectively. Detailed probe structure information, computer-predicted melting temperatures for the unlabeled probe sequences and measured melting temperatures for the labeled probes are listed in Table 1.

Synthesis of unlabeled oligonucleotides: All unlabeled oligonucleotides (primers) were synthesized by starting with a protected nucleoside on CPG support with a glass bead pore size of 500 Å. Deprotection, coupling and oxidation steps were all carried out by following standard protocols provided by the manufacturers. Cleavage of oligonucleotides from CPG support and deprotections were carried out by incubating the CPG beads in ammonium hydroxide at 55° C. for 16-18 hours. Once removed from the solid support, the oligonucleotides were concentrated down via a SpeedVac to remove the excess ammonia, and then purified by passing the crude products through a Sephadex G-25 column or a C18 reverse phase cartridge. Final purifications, if necessary, were carried out with HPLC (See Purification below).

Synthesis of Amine-functionalized Oligonucleotides: Amine-functionalized oligonucleotides were synthesized by using a CPG-supported amino modifier and appropriate phosphoramidite reagents containing a protected amine during the normal automated oligo synthesis. A variety of commercially available CPG-supported amino-modifiers with different spacer arms can be used. These products allow one to introduce an amino group at the 3' end. The CPG-supported amino modifier, 3'-amino-modifier C7 CPG, was used in some of the examples listed in Table 1 and it has the following structure:

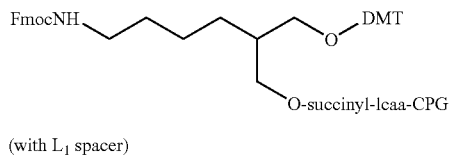

(with $L_1$ spacer)

wherein, Fmoc and DMT are protection groups for the amine and hydroxy groups, respectively, and "succinyl-lcaa" is a spacer between the solid support and the modifier. The base-labile Fmoc group was removed during ammonium treatment to remove oligos from CPG support. The reagent introduces a 7-carbon branched spacer between the amine group and the 3'-end phosphate. For reference purpose, we refer to this spacer as $L_1$. One skilled in the art can appreciate that there are many other forms of modifier reagents on a solid support that can be used to introduce an amine with a different spacer, or to introduce a different reactive group other than an amine.

Amine-containing phosphoramidite reagents include phosphoramidites of protected amino-deoxynucleosides and protected amino-modifiers. The most widely used and also least expensive phosphoramidites of protected amino-deoxynucleosides is phosphoramidite of trifluoroacetylamino-2'-deoxythymidine, or amino-modifier C6 dT, which was used for making T-modified oligonucleotides in some of the examples given Table 1. Shown below is the structure of amino-modifier C6 dT:

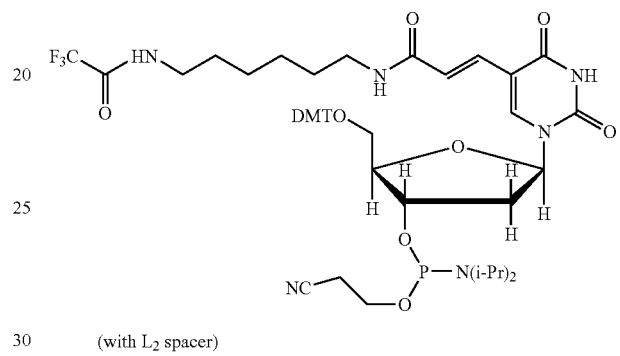

(with $L_2$ spacer)

This reagent introduces a 10-atom linear aliphatic spacer between dT and the amine group, or between dT and a dye. For reference purpose, we refer to the 10-atom spacer as $L_2$.

Alternatively, an amine can be introduced to the 5'-end by using a phosphoramidite of a protected amine at the last step of the automated synthesis. Two amino modifier reagents, 5'-amino-modifier C6-TFA and 5-amino-modifier C12, were used for synthesizing 5'-end labeled oligonucleotides shown in this disclosure. The structures are shown below:

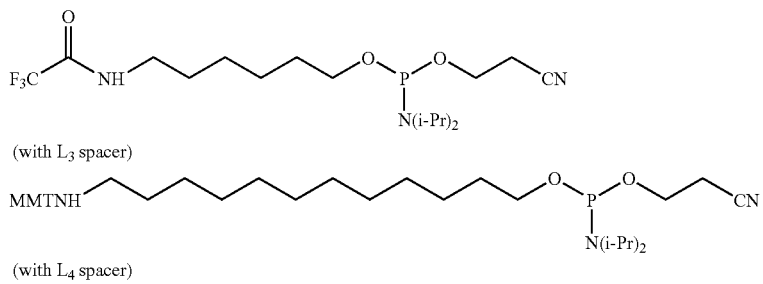

For reference purpose, the linear 6-carbon spacer of 5'-amino-modifier C6-TFA is referred to as $L_3$, and similarly the linear 12-carbon spacer of 5'-amino-modifier C12 is referred to as $L_4$.

There are many other forms of modifier reagents that can be used to introduce an amine into the backbone or bases of an oligonucleotide, or to introduce a different reactive group other than an amine.

Synthesis of probes with two identical labels: Labeling reactions were conducted by adding a solution of a succinimidyl ester dye (Biotium, Inc., Hayward, Calif.) in DMF at ~40 mg./mL to an amine-containing oligonucleotide dissolved in 0.1 M NaHCO$_3$ (pH 8.5) at ~1 mg/mL and vortexing the solution at room temperature for ~2 h. 5-carboxyrhodamine 110 SE (5-CR110SE) was used to conjugate rhodamine 110 (R110) to the oligonucleotides. Similarly, 5-carboxyrhodamine 6G SE (5-R6G SE) was used for conjugating rhodamine 6G (R6G) to the oligonucleotides. The molar ratio of dye NHS ester to each amino group in the oligonucleotide was about 20 to 1. Unreacted dye was effectively removed by a Sephadex G-25 spin column. The crude products thus obtained were subject to further purification by HPLC.

Purification of labeled oligonucleotide: Labeled oligonucleotides were purified by reverse phase HPLC on a Hitachi D7000 HPLC System. Listed below were typical protocols utilized in purifying the labeled oligonucleotides.
Typical HPLC condition:
Column: C18 YMC ODS-A 5 um 12 nm 150×4.6 mm, or C18 Microsorb 5 um 30 nm 200×4.6.
Column temperature: 45° C.
Gradient: 10% B to 50% B in 20 min-30 min @ 1 ml/min. A: 100 mM TEAA PH7.0; B: 100% CH$_3$CN.

Determination of degree of labeling for homo doubly-labeled probes: The absorbance from 230 nm to 700 nm of purified dye labeled oligonucleotides was measured on a spectrophotometer, whereby $\lambda_{max}$ for the dye ($A_{max}$) and $A_{260}$ were determined. The concentration of the dye was determined by measuring $A_{max}$ values, while the oligonucleotide concentration was calculated based on $A_{260}$ after factoring in the absorbance of the dye at 260 nm. The ratio of dye to oligonucleotide concentrations defines the degree of labeling (DOL). The DOL for homo dual labeled oligonucleotide probes is close to two. Based on this calculation, the dually labeled probes exhibit a purity of 90% to 95%.

Example 2

Real Time PCR:

All nucleic acid amplifications were performed in 20 μL reaction solution containing 10 mM Tris (pH 8.0), 50 mM KCl, 2.5 mM MgCl$_2$, 2 mM each of dNTP, and 1 unit of AmpliTaq Gold from ABI (Foster City, Calif.). Each template used in the amplification experiments was a gene fragment cloned in pTOPO plasmid (Invitrogen, Calsband, Calif.). All reactions were run with 10$^7$ copies of plasmid template and 0.5 μM each of a forward primer, a reverse primer, and a doubly labeled probe. For all reactions the thermal regimen was set at 95° C. for 10-minutes followed by 50 cycles of 15-second duration at 95° C. and 60-second duration at 60° C. Similarly, for all reactions fluorescence was measured at the 60° C. step with filter set of 490 nm/525 nm for 5-CR110 or FAM, 535 nm/575 nm for 5-R6G in BioRad IQ cycler.

Performance of varying length of GDH probes that are labeled with homo-dual 5-carboxy-rhodamine 110 dyes: CR*GDH-0*CR (SEQ ID No.5) was designed by PrimerExpress according to the conventional rule, i.e., Tm'+10° C. CR*GDH-8*CR (SEQ ID No.8) was designed according the present invention. CR*GDH-3*CR (SEQ ID No.6) and CR*GDH-6*CR (SEQ ID No.7) are two probes possessing with intermediate length and Tm. Five hundred nM of each of the four probes were used to monitor the PCR amplification of a pTOPO vector contain a GDH gene (SEQ ID No. 48) by GDHf (SEQ ID No.1) and GDHr (SEQ ID No.2) following the procedure method described herein. The amplification curves resulting from experiments using each of the four probes are shown in FIG. 1. The shortest probe, CR*GDH-8*CR (SEQ ID No.8) demonstrated even better performance in the real-time PCR amplification than the longer CR*GDH-0*CR (SEQ ID No.5).

Performance of various length HMB probes incorporating homo dual rhodamine 110 labels: CR*HMB-0*CR (SEQ ID No.17) was designed by PrimerExpress according to the conventional Tm'+10 rule. CR*HMB-2*CR (SEQ ID No.19) was designed according to the present invention. CR*HMB-3*CR (SEQ ID No.18) is a probe with length and Tm in between. Five hundred nM of each of the four probes were used to monitor the PCR amplification of a pTOPO vector contain a HMB gene (SEQ ID No. 49) by HMBf (SEQ ID No.15) and HMBr (SEQ ID No.16) following to the procedure described in Example 2. The amplification curves by each of the three probes were presented in FIG. 2. The results indicate that the shorter CR*HMB-4*CR provided high quality signal.

Performance of various length ABK probes incorporating homo dual rhodamine 110 labels: CR*ABK-0*CR (SEQ ID No.22) was designed by PrimerExpress according to the conventional rule of Tm+10° C. CR*ABK-6*CR (SEQ ID No.24) was designed according to the present invention. CR*ABK-3*CR (SEQ ID No.23) is a probe possessing intermediate length and Tm. CR*ABK-10*CR (SEQ ID No.25) is a probe of lower Tm. Five hundred nM of each of the three probes were used to monitor the PCR amplification of a pTOPO vector contain a ABK gene (SEQ ID No. 50) by ABKf (SEQ ID No. 20) and ABKr (SEQ ID No. 21) following to the procedure described in Example 2. The amplification curves resulting from experiments using each of the four probes were presented in FIG. 3. CR*ABK-6*CR (SEQ ID No.24) provided high quality signal in a real-time PCR amplification reaction.

Performance of various length GDH probes incorporating homo dual Rhodamine 6G labels: RG*GDH-0*RG (SEQ ID No.10) was designed by PrimerExpress according to the conventional Tm+10° C. rule. RG*GDH-8*RG (SEQ ID No.13) was designed according to the present invention. RG*GDH-3*RG (SEQ ID No.11) and RG*GDH-6*RG (SEQ ID No.12) are two probes possessing intermediate length and Tm. RG*GDH-11*RG (SEQ ID No.14) is a probe with lower Tm. Five hundred nM of each of the four probes were used to monitor the PCR amplification of a pTOPO vector contain a GDH gene (SEQ ID No. 48) by GDHf (SEQ ID No. 1) and GDHr (SEQ ID No. 2) following the procedure described herein. The amplification curves resulting from experiments utilizing each of the five probes were presented in FIG. 4. RG*GDH-8*RG (SEQ ID No.13) provided significantly better signal in the experiments than RG*GDH-0*RG (SEQ ID No.10).

Performance of various length BLI probes incorporating homo dual rhodamine 110 labels: CR*BLI-0*CR (SEQ ID No.44) was designed by PrimerExpress according to the conventional Tm+10° C. rule. CR*BLI-0*CR (SEQ ID No.45) was designed by the rule according to the present invention. FAM*BLI-0*TAM (SEQ ID No.46) and FAM*BLI-2*TAM (SEQ ID No.47) are regular TagMan® probes. Five hundred nM of each of the four probes were used to monitor the PCR amplification of a pTOPO vector contain a BLI gene (SEQ ID No. 51) by BLIf (SEQ ID No.52) and BLIr (SEQ ID No.53) following to the procedure described herein. The amplification curves resulting from experiments utilizing each of the 4 probes were presented in FIG. 5. CR*BLI-6*CR (SEQ ID No. 45) provided high quality signal to thus obtain rigorous results with an oligonucleotide with significantly truncated length.

Single mismatch discrimination by CR*GDH-8*CR: This experiment demonstrates that an exemplary probe prepared according to the present invention is capable of discriminate a single nucleotide mismatch via real-time PCR. CR*GDH-8*CR was used to test one wild type template and four mutant templates. The probe sequence and the template sequences that are covered by the probe are listed in the chart below:

| Name | Sequences | In Seq ID No. |
|---|---|---|
| Probe | CATGACCACAGTCCATGCC (bases 3-21 of SEQ ID NO: 7) | 7 |
| wt | CATGACCACAGTCCATGCC (bases 34-52 of SEQ ID NO: 48) | 48 |
| temp-A | CATGAACACAGTCCATGCC (bases 34-52 of SEQ ID NO: 54) | 54 |
| temp-T | CATGATCACAGTCCATGCC (bases 34-52 of SEQ ID NO: 55) | 55 |
| temp-G | CATGAGCACAGTCCATGCC (bases 34-52 of SEQ ID NO: 56) | 56 |
| temp-2mm | CATGAGCACAATCCATGCC (SEQ ID NO: 58) | 57 |

The single mismatched base was under line in the above chart. FIG. 6, Panel A shows the experimental result. Only the perfectly matched sequence was detected by the probe, whereas templates with even a single mismatch were not detected. The ability of the probes of the present invention to detect single nucleotide mismatch is comparable if not exceeding that of the conventional TaqMan® probe (Seq ID. 9, having FAM labeled at 5' end and a TAMRA labeled at the 3' end). See FIG. 6, Panel B.

Lack of inhibitory effect: The subject probes exhibit or minimal inhibition during a PCR reaction. See FIG. 7. In contrast, the conventional FAM*GAPDH*MGB can exhibit an inhibitory effect on real time PCR reactions. For example, the experiment in FIG. 7 shows a concentration-dependent inhibitory effect of 1×, 2× and 3× of GAPDH FAM/MGB labeled probe (FAM*GAPDH*MGB, ABI Cat #4352934E). As the concentration of the probe and primer increased, the increased concentration of the FAM/MGB labeled probe caused a delay in Ct, as well as a suppression in the level of final fluorescent signals. Under identical conditions, as the concentration of CR*GDH-8*CR of the present invention was increased by equivalent factors in the real time PCR reactions, the final fluorescent signals increased and Ct was not affected. Therefore, the probes of the present invention can yield more robust results and are more flexibility in assay conditions, especially those required for real time PCR reactions.

Melting curve analyses: In order to assess the relative affinity of the homo-dually labeled probes to their complementary strands, complementary strands to each of the homo-dually labeled probes were synthesized (Table 1), and hybrids were formed by mixing each labeled probe with the corresponding unlabeled complementary strand in 1:1 ratio at 1 µM in 20 µL reaction containing 10 mM Tris (pH 8.0), 50 mM KCl and 2.5 mM MgCl$_2$. The melting curves of the hybrids were measured. Prior to melting, samples were denatured at 95° C. for 5 min and then cool to 40° C. over a 30 min period (controlled by thermal programming of an IQ cycler). The hybrids were melted at a rate of 0.5° C./min. Fluorescence data were recorded at every half degree on a BioRad IQ cycler. It has been observed that all TaqMan® probes, which have a reporter dye and a quencher, like FAM*BLI-0*TAM, follows Foster theory. They stay in de-quenched state when duplexed with their complementary strands, and become quenched when duplexes melt (FAM*BLI-0*TAM in FIG. 12), exhibiting a positive melting curve in a typical melting plot where the x-axis is the temperature and the y-axis is −dF/dT (F is the fluorescence, and T is the temperature). In this experiment, the temperature corresponding to the peak of the melting curve is the Tm of the probe. FAM*BLI-0*TAM, a longer sequence relative to the probes of the present invention and designed using Primer Express, did not started to melt till around 70° C. (FIG. 12), as expected.

The probes designed according to the present invention behave differently. Some have positive melting curves (CR*TBP-9*CR in FIG. 11, CR*BLI-6*CR in FIG. 12), others have negative melting curves (CR*BAN*CR in FIG. 10, CR*GAP-6*CR in FIG. 8, RG*GAP-6*RG in FIG. 9), and some did not exhibit apparent melting curves (CR*TBP-9*CR in FIG. 11, CR*BLI-0*CR in FIG. 12). Therefore, the dequenching/quenching properties of these probes cannot be simply explained by Foster theory. CR*TBP-9*CR in FIG. 11 demonstrated duplex form from 40° C. to 58° C. It started to melt above 58° C. At 65° C., it was 50% in duplex form, and 50% in melted form. At 72° C. and above, it was completely dissociated from its complement. Although CR*GDH-8*CR, CR*TBP-9T*CR, or CR*BLI-6*CR, all designed according to the present invention, have calculated Tm's around 60° C., the respective melting curves showed that each of these probes remained nearly completely in duplex form at 60° C. (See FIGS. 8, 11, and 12 respectively). These probes only began to melt beginning from around 60° C.

All publications, patents, and patent applications cited in this specification are incorporated herein by reference as if each individual publication, patent, or patent application was specifically and individually indicated to be incorporated by reference and set forth in its entirety herein.

Unless specifically identified to the contrary, all terms used herein are used to include their ordinary and customary terminology. Further, while various embodiments of diagnostic tests and medical treatment devices having specific components and steps are described and illustrated herein, it is to be understood that any selected embodiment can include one or more of the specific components and/or steps described for another embodiment where possible.

Further, any theory of operation, proof, or finding stated herein is meant to further enhance understanding of the present invention and is not intended to make the scope of the present invention dependent upon such theory, proof, or finding.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected. And while the invention was illustrated using specific examples, and theoretical arguments, protein and DNA sequences, accounts and illustrations these examples, arguments, illustrations sequences, accounts and the accompanying discussion should by no means be interpreted as limiting the invention. The Abstract of the Disclosure is included for the convenience of the persons searching for the document; the Abstract is not a summary of the invention it should not be used to interpret or to limit the claims or specification.

TABLE 1

| SEQ ID | Oligonucleotide Name[1] | Type | Length | $T_m$ (° C.) (calculated for unlabeled probes)[2] | $T_m$ (° C.) (measured for labeled probes)[3] | Sequence Detail[4] |
|---|---|---|---|---|---|---|
| 1 | GDHf | primer | 24 | 59 | | 5'-CATCCATGACAACTTTGGTATCGT-3' |
| 2 | GDHr | primer | 21 | 62 | | 5'-CAGTCTTCTGGGTGGCAGTGA-3 |
| 3 | GDHc | complement | 27 | 66 | | 5'-GGCATGGACTGTGGTCATGAGTCCTTC-3' |
| 4 | GDH-0 | unlabeled probe | 27 | 66 | | 5'-GAAGGACTCATGACCACAGTCCATGCC-3' |
| 5 | CR*GDH-0*CR | probe | 27 | 66 | 70 | 5'-(5-CR110-L$_1$-)GAAGGACTCATGACCACAGTCCATGCC(-L$_1$-5-CR110)-3' |
| 6 | CR*GDH-3*CR | probe | 24 | 65 | 76 | 5'-(5-CR110-L$_3$-)GGACTCATGACCACAGTCCATGCC(-L$_1$-5-CR110)-3' |
| 7 | CR*GDH-6*CR | probe | 21 | 61 | 76 | 5'-(5-CR110-L$_3$-)CTCATGACCACAGTCCATGCC(-L$_1$-5-CR110)-3' |
| 8 | CR*GDH-8*CR | probe | 19 | 59 | 72.5 | 5'-(5-CR110-L$_3$-)CATGACCACAGTCCATGCC(-L$_1$-5-CR110)-3' |
| 9 | FAM*GDH-8*TAM | probe | 19 | 59 | | 5'-(FAM-L$_3$-)CATGACCACAGTCCATGCC(-L$_1$-TAMRA)-3' |
| 10 | RG*GDH-0*RG | probe | 27 | 66 | 75 | 5'-(5-R6G-L$_3$-)GAAGGACTCATGACCACAGTCCATGCC(-L$_1$-5-R6G)-3' |
| 11 | RG*GDH-3*RG | probe | 24 | 65 | undetectable | 5'-(5-R6G-L$_3$-)GGACTCATGACCACAGTCCATGCC(-L$_1$-5-R6G)-3' |
| 12 | RG*GDH-6*RG | probe | 21 | 61 | 71.5 | 5'-(5-R6G-L$_3$-)CTCATGACCACAGTCCATGCC(-L$_1$-5-R6G)-3' |
| 13 | RG*GDH-8*RG | probe | 19 | 59 | 70.5 | 5'-(5-R6G-L$_3$-)CATGACCACAGTCCATGCC(-L$_1$-5-R6G)-3' |
| 14 | RG*GDH-11*RG | probe | 16 | 56 | | 5'-(5-R6G-L$_3$-)GACCACAGTCCATOCC(-L$_1$-5-R6G)-3' |
| 15 | HMBf | primer | 20 | 60 | | 5'-TGCAGGCTACCATCCATGTC-3' |
| 16 | HMBr | primer | 22 | 61 | | 5'-CCTACCAACTGTGGGTCATCCT-3 |
| 17 | CR*HMB-0*CR | probe | 22 | 66 | | 5'-(5-CR110-L$_3$-)CTGCCCAGCATGAAGATGCCC(-L$_1$-5-CR110)-3' |
| 18 | CR*HMB-2*CR | probe | 20 | 64 | | 5'-(5-CR110-L$_3$-)GCCCAGCATGAAGATGGCCC(-L$_1$-5-CR110)-3' |
| 19 | CR*HMB-4*CR | probe | 18 | 60 | | 5'-(5-CR110-L$_3$-)GCCCAGCATGAAGATGGC(-L$_1$-5-CR110)-3' |
| 20 | ABKf | primer | 24 | 59 | | 5'-TCTCTGAAGGGAGTTTCTCCAATT-3' |
| 21 | ABKr | primer | 23 | 60 | | 5'-TTCACACAGTGGTTTGGCTTAGA-3 |

TABLE 1-continued

| SEQ ID | Oligonucleotide Name[1] | Type | Length | $T_m$ (° C.) (calculated for unlabeled probes)[2] | $T_m$ (° C.) (measured for labeled probes)[3] | Sequence Detail[4] |
|---|---|---|---|---|---|---|
| 22 | CR*ABK-0*CR | probe | 28 | 64 | | 5'-(5-CR110-L$_3$-)TTTGGACCACCATTGCAGAGTTCTTC(-L$_1$-5-CR110)-3' |
| 23 | CR*ABK-3*CR | probe | 25 | 63 | | 5'-(5-CR110-L$_3$-)GGACCCACCATTGCAGAGTTCTTC(-L$_1$-5-CR110)-3' |
| 24 | CR*ABK-6*CR | probe | 22 | 61 | | 5'-(5-CR110-L$_3$-)GGACCCACCATTGCAGAGTTC(-L$_1$-5-CR110)-3' |
| 25 | CR*ABK-10*CR | probe | 18 | 58 | | 5'-(5-CR110-L$_3$-)GGACCCACCATTGCAGAG(-L$_1$-5-CR110)-3' |
| 26 | APBc | complement | 30 | 59 | | 5'-AAATTT CCCACCATATAGAAGGCC ATATAT-3' |
| 27 | APB | unlabeled probe | 18 | 55 | | 5'-GGCCTTCTATATGTGGG-3' |
| 28 | CR*APB*CR | probe | 18 | 55 | 64 | 5'-(5-CR110-L$_3$-)GGCCTTCTATATGTGGG(-L$_1$-5-CR110)-3' |
| 29 | RG*APB*RG | probe | 18 | 55 | | 5'-(5-R6G-L$_3$-)GGCCTTCTATATGTGGG(-L$_1$-5-R6G)-3' |
| 30 | BANc | complement | 27 | 62 | | 5'-ATATAT GCGCTCAGGAGGAGC AAATTT-3' |
| 31 | BAN | unlabeled probe | 15 | 58 | | 5'-GCTCCTCCTGAGCGC-3' |
| 32 | CR*BAN*CR | probe | 15 | 58 | 76 | 5'-(5-CR110-L$_3$-)GCTCCTCCTGAGCGC(-L$_1$-5-CR110)-3' |
| 33 | HPRc | complement | 26 | 61 | | 5'-TATATA CACGACGCCAGGGC TTTAAA-3' |
| 34 | HPR | unlabeled probe | 14 | 59 | | 5'-GCCCTGGCGTCGTG-3' |
| 35 | CR*HPR*CR | probe | 14 | 59 | 69 | 5'-(5-CR110-L$_3$-)GCCCTGGCGTCGTG(-L$_1$-5-CR110)-3' |
| 36 | TBPc | complement | 46 | 72 | | 5'-GGGGCCAACCAGAAATAACTCTGGCTCATAACTACTAAAGCGCGC-3' |
| 37 | TBP | unlabeled probe | 34 | 62 | | 5'-TTTAGTAGTTATGAGCCAGAGTTATTTCCTGGTT-3' |
| 38 | CR*TBP-0*CR | probe | 34 | 62 | undetectable | 5'-(5-CR110-L$_3$-)TTTAGTAGTTATGAGCCAGAGTTATTTCCTGGTT(-L$_1$-5-CR110)-3' |
| 39 | CR*TBP-9*CR | probe | 25 | 59 | | 5'-(5-CR110-L$_3$-)GTTATGAGCCAGAGTTATTTCCTGG(-L$_1$-5-CR110)-3' |
| 40 | CR*TBP-9T*CR | probe | 25 | 59 | 65 | 5'-(5-CR110-L$_3$-)GTTATGAGCCAGAGT(-L$_2$-5-CR110)TATTTCCTGGp-3' |
| 41 | CR*TBP-14*CR | probe | 20 | 56 | 66 | 5'-(5-CR110-L$_3$-)GAGCCAGAGTTATTTCCTGG(-L$_1$-5-CR110)-3' |
| 42 | BLIc | complement | 37 | 66 | | 5'-TTTAAA AGACCCCACACTACCATCGGCGCTA ATATAT-3' |

TABLE 1-continued

| SEQ ID NO | Oligonucleotide Name[1] | Type | Length | $T_m$ (°C.) (calculated for unlabeled probes)[2] | $T_m$ (°C.) (measured for labeled probes)[3] | Sequence Detail[4] |
|---|---|---|---|---|---|---|
| 43 | BLI | unlabeled probe | 25 | 68 | | 5'-TAGCGCCCATGTAGTGTGGGGTCT-3' |
| 44 | CR*BLI-0*CR | probe | 25 | 68 | undetectable | 5'-(5-CR110-L$_3$-)TAGCGCCCATGGTAGTGTGGGGTCT(-L$_1$-5-CR110)-3' |
| 45 | CR*BLI-6*CR | probe | 19 | 60 | 70 | 5'-(5-CR110-L$_3$-)TAGCGCCCATGGTAGTGTG(-L$_1$-5-CR110)-3' |
| 46 | FAM*BLI-0*TAM | probe | 25 | 68 | | 5'-(FAM)-TAGCGCCCATGTAGTGTGGGGTCT-(TAMRA)-3' |
| 47 | FAM*BLI-2*TAM | probe | 23 | 67 | | 5'-(FAM)-TAGCGCCCATGGTAGTGTGGGGT-(TAMRA)-3' |
| 48 | GDH gene | insert in plasmid | 74 | | | CATCCATGACAACTTTGGTATCGTGGAAGGACTCATG ACCACAGTCCATGCCATCACTGCCACCCAGAAGACTG |
| 49 | HMB gene | insert in plasmid | 249 | | | GTCTAGACGGCTCAGATAGCATACAAGAGACCATGCA GGCTACCATCCATGTCCCTGCCCAGCATGAAGATGGC CCTGAGGATGACCCACAGTTGGTAGGCATCACTGCTC GTAACATTCCACGAGGGCCCCAGTTGCTGCCCAGAA CTTGGGCATCAGCCTGGCCAACTTGTTGCTGAGCAAA GGAGCCAAAAACATCCTGGATGTTGCACGGCAGCTTA ACGATGCCCATTAACTGGTTTGTGGGG |
| 50 | ABK gene | insert in plasmid | 84 | | | TCTCTGAAGGGAGTTTCTCCAATTATTTGGACCCACCA TTGCAGAGTTTCTTCAGTTAGGTCTAAGCCAAACCACT GTGTGAAC |
| 51 | BLI gene | insert in plasmid | 86 | | | CCCCATGCCGAACTCAGAAGTGAAACGCCCTAGCGCC GATGGTAGTGTGGGGTCTCCTCATGCGAGAGTAGGGA ACTGCCAGGCAT |

TABLE 1-continued

Sequence Information

| SEQ ID NO | Oligonucleotide Name[1] | Type | Length | $T_m$ (°C.) (calculated for unlabeled probes)[2] | $T_m$ (°C.) (measured for labeled probes)[3] | Sequence Detail[4] |
|---|---|---|---|---|---|---|
| 52 | BLIf | | 16 | | | CCCCATGCCGAACTCA |
| 53 | BLIr | | 18 | | | ATGCCTGGCAGTTCCCTAC |
| 54 | TempA of GDH gene | insert in plasmid | 74 | | | CATCCATGACAACTTTGGTATCGTGAAGGACTCATG |
| | | | | | | AACACAGTCCATGCCATCACTGCCACCCAGAAGACTG |
| 55 | TempT of GDH gene | insert in plasmid | 74 | | | CATCCATGACAACTTTGGTATCGTGAAGGACTCATG |
| | | | | | | ATCACAGTCCATGCCATCACTGCCACCCAGAAGACTG |
| 56 | TempG of GDH gene | insert in plasmid | 74 | | | CATCCATGACAACTTTGGTATCGTGAAGGACTCATG |
| | | | | | | AGCACAGTCCATGCCATCACTGCCACCCAGAAGACTG |
| 57 | Temp2mm of GDH gene | insert in plasmid | 74 | | | CATCCATGACAACTTTGGTATCGTGAAGGACTCATG |
| | | | | | | AGCACACTCCATGCCATCACTGCCACCCAGAAGACTG |

[1]Each probe name consists of the name of the gene in the middle, a numerical number following the gene-name indicating the number of nucleotides removed from the parent/conventional probe sequence, two "*" symbols indicating the linkage between each label and the oligonucleotidenucleotide, and abbreviated name of the dye at the beginning and end of the probe name. In the name of SEQ ID NO: 40, the letter "T" following the number "9" indicates that one of the reporter dye CR110 is attached internally through a base T as shown in the sequence information. CR, RG, FAM and TAM are the abbreviations for rhodamine 110, rhodamine 6G, fluorescein and tetramethylrhodamine (TAMRA), respectively.
[2]Calculated Tm of unmodified oligonucleotidenucleotides. Calculation was based on the nearest-neighbor two-state model, which is applicable to short DNA duplexes. (SantaLucia, J., Jr., Proc. Natl. Acad. Sci. (P.N.A.S.) vol 95, pp 1460-1465, 1998). Sixty mM of monovalent salt concentration and 500 nM of the oligonucleotidenucleotide were used as default conditions.
[3]Observed Tm of labeled probes. Tm of each probe was determined from the melt curve of the hybrid formed between the probe and its complementary strand using a Bio-Rad IQ cycler. "Undetectable" means that the melting curve did not show any significant peak to allow estimate of the melting temperature. (Example 2).

What is claimed is:

1. A dually labeled oligonucleotide probe for an amplification reaction that hybridizes to a region in a target nucleic acid, said probe comprising a first dye that is fluorescent and a second dye, separated by at least about 5 nucleotide bases, wherein:
   (a) the two dyes are configured in a manner such that the first dye acts as a reporter that contributes to a fluorescent signal detected after hybridization of the probe with the target nucleic acid, and the second dye acts as a quencher of the first dye; and
   (b) at least one of the two dyes enhances probe hybridization such that the probe has a calculated melting temperature (calculated Tm) that is no more than 5° C. higher than that of a primer used in conjunction with the probe in amplifying the target nucleic acid in the amplification reaction; and wherein the primer used in conjunction with the probe has a calculated Tm within the range of about 45° C. and about 70° C.

2. The probe for an amplification reaction according to claim 1, wherein the probe has a calculated melting temperature (calculated Tm) that is within ±5° C. of a calculated Tm of a primer used in conjunction with the probe in amplifying the target nucleic acid.

3. The probe for an amplification reaction according to claim 1, wherein the probe has a calculated melting temperature (calculated Tm) that is substantially the same or lower as compared to a calculated Tm of a primer used in conjunction with the probe in amplifying the target nucleic acid.

4. The probe for an amplification reaction of any claims of 1, 2 and 3, wherein Tm is calculated based on a method of SantaLucia setting a salt concentration at 60 mM and a concentration of the oligonucleotide at 500 nm.

5. The probe for an amplification reaction according to claim 1, wherein the second dye is a fluorescent dye.

6. The probe for an amplification reaction of claim 1, wherein the quencher quenches the reporter dye when the probe is not hybridized with the target nucleic acid.

7. The probe for an amplification reaction according to claim 1, wherein one of the two dyes is attached to the 3'-terminus and the other dye is attached to the 5'-terminus of the probe.

8. The probe for an amplification reaction according to claim 1, wherein the first dye and the second dye have the same chemical structure.

9. The probe for an amplification reaction according to claim 1, wherein the second dye contributes to the fluorescent signal detected after hybridization of the probe with the target nucleic acid and after cleavage of the second dye from the probe.

10. The probe for an amplification reaction according to claim 1, wherein the at least one of the two dyes is selected from the group consisting of a rhodamine dye, a positively charged cyanine dye, a rosamine dye, an oxazine dye and a thiazine dye.

11. The probe for an amplification reaction of claim 10, wherein the rhodamine dye has the structural formula of:

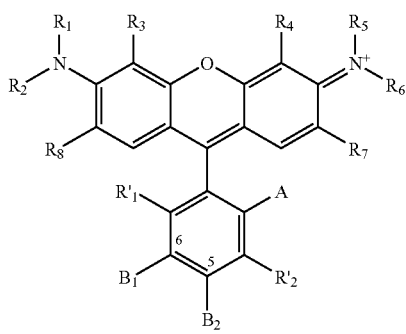

wherein $R_1$-$R_8$ are H or C1-C3 alkyl, where each pair of $R_1$ and $R_2$, $R_2$ and $R_8$, $R_1$ and $R_3$, $R_4$ and $R_5$, $R_5$ and $R_6$, and $R_6$ and $R_7$, optionally and independently forms a 5- or 6-membered ring, wherein the 5- or 6 membered ring optionally comprises one double bond and/or one or more C1-C2 alkyl substituents; A is —$CO_2^-$ or —$SO_3^-$; $R'_1$ and $R'_2$ are each independently H, F or Cl; one of $B_1$ and $B_2$ represents the attachment site of the oligonucleotide, and the reminder of $B_1$ and $B_2$ is H, F or Cl.

12. The probe for an amplification reaction of claim 10, wherein the positively charged cyanine dye has the structural formula of:

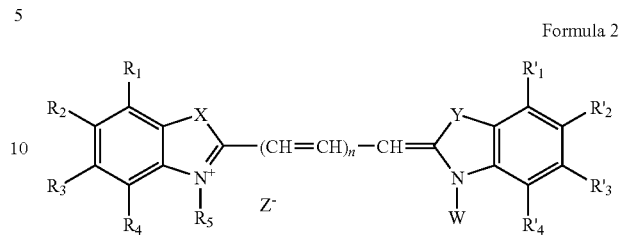

Formula 2 wherein each of $R_1$-$R_4$ and $R'_1$-$R'_4$ is independently selected from H, C1-C4 alkyl, F, Cl and Br; alternatively, each pair of $R_1$ and $R_2$ and/or $R'_1$ and $R'_2$ independently forms a fused benzene ring; $R_5$ is a C1-C3 alkyl; X and Y are independently selected from $C(CH_3)_2$, O, S and $NR_6$, where $R_6$ is a C1-C2 alkyl; n is selected from 1, 2 and 3; $Z^-$ is an anion for balancing the positive charge of the dye; and W represents the attachment site of the oligonucleotide.

13. The probe for an amplification reaction according to claim 1, wherein the first dye and the second dye do not form a FRET pair.

14. The probe for an amplification reaction according to claim 1, wherein the first dye and/or the second dye are attached to an internal base thymidine (T).

15. The probe for an amplification reaction according to claim 1, wherein the probe yields an undetectable gain of fluorescent intensity when hybridized to a target nucleic acid and prior to cleavage by a polymerase used in conjunction in an amplification reaction.

16. The probe for an amplification reaction according to claim 1, wherein the probe exhibits a decrease in fluorescent intensity when hybridized to a target nucleic acid and prior to cleavage by a polymerase used in conjunction in an amplification reaction.

17. The probe for an amplification reaction according to claim 1, wherein the probe comprises between about 5 to about 15 nucleotides.

18. A reaction mixture useful for amplification of a target nucleic acid comprises at least one oligonucleotide primer and a probe for an amplification reaction of claim 1, wherein the primer primes the synthesis of a strand of the target nucleic acid, and wherein the probe hybridizes to a region of the target nucleic acid synthesizable by said primer.

19. The reaction mixture of claim 18 further comprising a nucleic acid polymerase having a 5' to 3' nuclease activity.

20. The reaction mixture of claim 18 comprising a forward primer and a reverse primer that are complementary to the target nucleic acid.

21. A kit for detecting a nucleic acid sequence comprising a reaction mixture of claim 17 and a nucleic acid polymerase.

* * * * *

UNITED STATES PATENT AND TRADEMARK OFFICE
CERTIFICATE OF CORRECTION

PATENT NO.       : 8,354,523 B2  
APPLICATION NO. : 12/307358  
DATED            : January 15, 2013  
INVENTOR(S)      : Mao et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 855 days.

Signed and Sealed this

First Day of September, 2015

Michelle K. Lee
*Director of the United States Patent and Trademark Office*